(12) United States Patent
Grace et al.

(10) Patent No.: US 10,492,863 B2
(45) Date of Patent: Dec. 3, 2019

(54) LASER ENERGY DELIVERY DEVICES INCLUDING LASER TRANSMISSION DETECTION SYSTEMS AND METHODS

(71) Applicant: The Spectranetics Corporation, Colorado Springs, CO (US)

(72) Inventors: Kenneth P. Grace, Woodland Park, CO (US); George Woodrow Burton, Colorado Springs, CO (US); Gregory Conway Ebbets, Colorado Springs, CO (US); Nolan Miller Horrall, Colorado Springs, CO (US); Brandon Thomas Hendrick, Colorado Springs, CO (US); Thomas Kelby Triffo, Colorado Springs, CO (US); Blaine Andrew Schneider, Colorado Springs, CO (US); Joseph Nicholas Matterson, Colorado Springs, CO (US); Weston Lee, Colorado Springs, CO (US); Donald R. Sandmore, Peyton, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 31 days.

(21) Appl. No.: 15/392,987

(22) Filed: Dec. 28, 2016

(65) Prior Publication Data

US 2017/0105801 A1     Apr. 20, 2017

Related U.S. Application Data

(63) Continuation-in-part of application No. 14/925,348, filed on Oct. 28, 2015, now Pat. No. 9,907,614.
(Continued)

(51) Int. Cl.
*A61B 18/24* (2006.01)
*A61B 18/20* (2006.01)
(Continued)

(52) U.S. Cl.
CPC ............ *A61B 18/245* (2013.01); *A61B 18/20* (2013.01); *A61B 2017/00535* (2013.01);
(Continued)

(58) Field of Classification Search
CPC ........... A61B 2017/00535; A61B 2017/00422; A61B 2018/20357; A61B 2018/00208
(Continued)

(56) References Cited

U.S. PATENT DOCUMENTS 4,053,845 A   10/1977 Gould
4,445,892 A   5/1984 Hussein et al.
(Continued)

FOREIGN PATENT DOCUMENTS

EP   165301 B1   4/1991
EP   2015672 B1   1/2009
(Continued)

OTHER PUBLICATIONS

Extended Search Report for European Patent Application No. 09833795.9 dated Apr. 12, 2012 6 pages.
(Continued)

*Primary Examiner* — Gary Jackson
*Assistant Examiner* — Zahed Kabir

(57) ABSTRACT

Laser energy delivery devices and methods are provided. A laser energy delivery device may include a housing, and a coupling is carried by the housing and adapted to couple to a laser energy generator. A sheath is carried by the housing, and the sheath includes a distal end adapted to be disposed in the subject. A plurality of transport members are carried by the sheath, and the plurality of transport members are adapted to receive laser energy at the coupling, transmit laser energy through the sheath, and deliver laser energy to the subject. A fluid-driven motor is carried by the housing and adapted to be driven upon receiving a fluid from a fluid
(Continued)

source. A drive wire is carried by the sheath and eccentrically coupled to the distal end of the sheath, and the drive wire is adapted to be rotatably driven by the fluid-driven motor and rotates to eccentrically rotate the distal end of the sheath.

13 Claims, 25 Drawing Sheets

Related U.S. Application Data

(60) Provisional application No. 62/199,431, filed on Jul. 31, 2015, provisional application No. 62/072,323, filed on Oct. 29, 2014.

(51) Int. Cl.
   *A61B 18/00* (2006.01)
   *A61B 17/00* (2006.01)

(52) U.S. Cl.
   CPC .............. *A61B 2018/00172* (2013.01); *A61B 2018/00208* (2013.01); *A61B 2018/00422* (2013.01); *A61B 2018/00577* (2013.01); *A61B 2018/00642* (2013.01); *A61B 2018/00779* (2013.01); *A61B 2018/00916* (2013.01); *A61B 2018/2005* (2013.01); *A61B 2018/20357* (2017.05)

(58) Field of Classification Search
   USPC .......................................................... 606/46
   See application file for complete search history.

(56) References Cited

U.S. PATENT DOCUMENTS

| | | | |
|---|---|---|---|
| 4,641,912 A | 2/1987 | Goldenberg | |
| 4,669,467 A | 6/1987 | Willett et al. | |
| 4,686,979 A | 8/1987 | Gruen et al. | |
| 4,732,448 A | 3/1988 | Goldenberg | |
| 4,747,405 A | 5/1988 | Leckrone | |
| 4,784,132 A | 11/1988 | Fox et al. | |
| 4,799,754 A | 1/1989 | Goldenberg | |
| 4,807,620 A | 2/1989 | Strul et al. | |
| 4,830,460 A | 5/1989 | Goldenberg | |
| 4,844,062 A | 7/1989 | Wells | |
| 4,848,336 A | 7/1989 | Fox et al. | |
| 4,886,496 A | 12/1989 | Conoscenti et al. | |
| 4,924,863 A | 5/1990 | Sterzer | |
| 5,016,964 A | 5/1991 | Donnelly | |
| 5,040,548 A | 8/1991 | Yock | |
| 5,041,108 A | 8/1991 | Fox et al. | |
| 5,042,976 A | 8/1991 | Ishitsu et al. | |
| 5,188,632 A | 2/1993 | Goldenberg | |
| 5,250,045 A | 10/1993 | Bohley | |
| 5,250,069 A | 10/1993 | Nobuyoshi et al. | |
| 5,263,952 A | 11/1993 | Grace et al. | |
| 5,263,953 A | 11/1993 | Bagby | |
| 5,300,085 A | 4/1994 | Yock | |
| 5,304,171 A | 4/1994 | Gregory et al. | |
| 5,350,375 A | 9/1994 | Deckelbaum et al. | |
| 5,350,395 A | 9/1994 | Yock | |
| 5,352,197 A | 10/1994 | Hammersmark et al. | |
| 5,415,653 A | 5/1995 | Wardle et al. | |
| 5,429,604 A * | 7/1995 | Hammersmark | A61B 18/245 600/182 |
| 5,429,617 A | 7/1995 | Hammersmark et al. | |
| 5,451,233 A | 9/1995 | Yock | |
| 5,456,680 A | 10/1995 | Taylor et al. | |
| 5,470,330 A | 11/1995 | Goldenberg et al. | |
| 5,484,433 A | 1/1996 | Taylor et al. | |
| 5,514,128 A | 5/1996 | Hillsman et al. | |
| 5,571,151 A | 11/1996 | Gregory | |
| 5,573,531 A | 11/1996 | Gregory | |
| 5,623,940 A | 4/1997 | Daikuzono | |
| 5,643,251 A | 7/1997 | Hillsman et al. | |
| 5,649,923 A | 7/1997 | Gregory et al. | |
| 5,693,043 A * | 12/1997 | Kittrell | A61B 1/00096 606/15 |
| 5,722,972 A | 3/1998 | Power et al. | |
| 5,725,521 A | 3/1998 | Mueller | |
| 5,817,144 A | 10/1998 | Gregory | |
| 5,824,026 A | 10/1998 | Diaz | |
| 5,836,946 A | 11/1998 | Diaz et al. | |
| RE36,104 E | 2/1999 | Solar | |
| 5,976,124 A | 11/1999 | Reiser | |
| 5,989,243 A | 11/1999 | Goldenberg | |
| 5,997,571 A | 12/1999 | Farr et al. | |
| 6,022,342 A | 2/2000 | Mukherjee | |
| 6,027,460 A | 2/2000 | Shturman | |
| 6,036,715 A | 3/2000 | Yock | |
| 6,066,130 A | 5/2000 | Gregory et al. | |
| 6,090,118 A | 7/2000 | McGuckin et al. | |
| 6,117,128 A | 9/2000 | Gregory | |
| 6,210,393 B1 | 4/2001 | Brisken | |
| 6,290,668 B1 | 9/2001 | Gregory et al. | |
| 6,290,710 B1 | 9/2001 | Cryer et al. | |
| 6,451,036 B1 | 9/2002 | Heitzmann et al. | |
| 6,458,098 B1 | 10/2002 | Kanesaka | |
| 6,554,794 B1 | 4/2003 | Mueller et al. | |
| 6,575,993 B1 | 6/2003 | Yock | |
| 6,602,264 B1 | 8/2003 | McGuckin et al. | |
| 6,613,038 B2 | 9/2003 | Bonutti et al. | |
| 6,743,208 B1 | 6/2004 | Coyle | |
| 6,824,550 B1 | 11/2004 | Noriega et al. | |
| 6,872,206 B2 | 3/2005 | Edwards et al. | |
| 7,037,316 B2 | 5/2006 | McGuckin et al. | |
| 7,090,683 B2 | 8/2006 | Brock et al. | |
| 7,169,141 B2 | 1/2007 | Brock et al. | |
| 7,214,230 B2 | 5/2007 | Brock et al. | |
| 7,252,664 B2 | 8/2007 | Nasab et al. | |
| 7,329,223 B1 | 2/2008 | Ainsworth et al. | |
| 7,371,210 B2 | 5/2008 | Brock et al. | |
| 7,507,246 B2 | 3/2009 | McGuckin et al. | |
| 7,628,763 B2 | 12/2009 | Noriega et al. | |
| 7,674,253 B2 | 3/2010 | Fisher et al. | |
| 7,744,608 B2 | 6/2010 | Lee et al. | |
| 7,758,569 B2 | 7/2010 | Brock | |
| 7,789,875 B2 | 9/2010 | Brock et al. | |
| 7,930,065 B2 | 4/2011 | Larkin et al. | |
| 8,043,314 B2 | 10/2011 | Noriega et al. | |
| 8,052,704 B2 | 11/2011 | Olson | |
| RE43,328 E | 4/2012 | Foley et al. | |
| 8,353,922 B2 | 1/2013 | Noriega et al. | |
| 8,409,136 B2 | 4/2013 | Wallace et al. | |
| 8,414,505 B1 | 4/2013 | Weitzner et al. | |
| 8,469,979 B2 | 6/2013 | Olson | |
| 8,496,680 B2 | 7/2013 | Noriega et al. | |
| 8,641,705 B2 | 2/2014 | Leo et al. | |
| 8,684,952 B2 | 4/2014 | Weitzner et al. | |
| 8,747,332 B2 | 6/2014 | Noriega et al. | |
| 8,821,483 B2 | 9/2014 | Boutoussov et al. | |
| 8,920,402 B2 | 12/2014 | Nash et al. | |
| RE45,484 E | 4/2015 | Foley et al. | |
| 9,028,489 B2 | 5/2015 | Choi | |
| 9,028,499 B2 | 5/2015 | Keyak et al. | |
| 9,060,793 B2 | 6/2015 | Larkin et al. | |
| 9,066,742 B2 | 6/2015 | Splinter | |
| 9,084,623 B2 | 7/2015 | Gomez et al. | |
| 9,084,624 B2 | 7/2015 | Larkin et al. | |
| 9,095,681 B2 | 8/2015 | Wenderow et al. | |
| 9,101,380 B2 | 8/2015 | Larkin et al. | |
| 9,113,955 B2 | 8/2015 | Noriega et al. | |
| 9,119,609 B2 | 9/2015 | O'Sullivan et al. | |
| 9,125,562 B2 | 9/2015 | Spencer et al. | |
| 9,125,679 B2 | 9/2015 | Larkin et al. | |
| 9,168,356 B2 | 10/2015 | Wenderow et al. | |
| 9,173,713 B2 | 11/2015 | Hart et al. | |
| 9,237,920 B2 | 1/2016 | Leo et al. | |
| 9,241,733 B2 | 1/2016 | Olson | |
| 9,254,143 B2 | 2/2016 | Huynh et al. | |
| 9,261,259 B2 | 2/2016 | Shiomi et al. | |
| 9,289,173 B2 | 3/2016 | Splinter | |

(56) References Cited

U.S. PATENT DOCUMENTS

| | | |
|---|---|---|
| 9,289,258 B2 | 3/2016 | Cohen |
| 9,351,726 B2 | 5/2016 | Leimbach et al. |
| 9,351,727 B2 | 5/2016 | Leimbach et al. |
| 9,351,789 B2 | 5/2016 | Novichenok et al. |
| D775,728 S | 1/2017 | Cavada et al. |
| 9,649,159 B2 | 5/2017 | Keeler |
| 2002/0151879 A1 | 10/2002 | Loeb |
| 2002/0188313 A1 | 12/2002 | Johnson et al. |
| 2003/0055398 A1 | 3/2003 | Imran |
| 2003/0083607 A1* | 5/2003 | Bobo, Jr. ............... A61B 18/24 604/20 |
| 2004/0015159 A1 | 1/2004 | Slater et al. |
| 2004/0079429 A1 | 4/2004 | Miller et al. |
| 2006/0094930 A1 | 5/2006 | Sparks et al. |
| 2006/0167442 A1 | 7/2006 | Hebert et al. |
| 2006/0206182 A1 | 9/2006 | Pyles |
| 2007/0270787 A1 | 11/2007 | Winston et al. |
| 2007/0299496 A1 | 12/2007 | Podmore et al. |
| 2008/0009673 A1 | 1/2008 | Khachi |
| 2008/0154345 A1 | 6/2008 | Taylor |
| 2008/0249515 A1 | 10/2008 | Taylor |
| 2008/0306499 A1 | 12/2008 | Katoh et al. |
| 2009/0105686 A1 | 4/2009 | Snow et al. |
| 2009/0254072 A1 | 10/2009 | Khatib et al. |
| 2010/0114081 A1 | 5/2010 | Keeler et al. |
| 2010/0137892 A1 | 6/2010 | Krolik et al. |
| 2011/0292378 A1 | 12/2011 | Brown |
| 2011/0319885 A1 | 12/2011 | Skwarek et al. |
| 2013/0023770 A1* | 1/2013 | Courtney ............... A61M 25/10 600/467 |
| 2013/0096545 A1 | 4/2013 | Laudenslager et al. |
| 2013/0289672 A1 | 10/2013 | Hakomori et al. |
| 2014/0031800 A1 | 1/2014 | Ben Oren et al. |
| 2014/0171943 A1* | 6/2014 | Weitzner ............ A61M 25/0113 606/41 |
| 2014/0276594 A1 | 9/2014 | Tanner et al. |
| 2014/0276689 A1* | 9/2014 | Grace ................ A61B 18/245 606/12 |
| 2015/0032024 A1* | 1/2015 | Furlong ................ A61B 10/04 600/563 |
| 2015/0073340 A1* | 3/2015 | Pacheco ................ A61B 34/30 604/95.01 |
| 2015/0150587 A1 | 6/2015 | Smith et al. |
| 2015/0201918 A1* | 7/2015 | Kumar ............... A61B 17/1622 606/104 |
| 2015/0272664 A9 | 10/2015 | Cohen |
| 2015/0342681 A1 | 12/2015 | Lee |
| 2015/0349480 A1 | 12/2015 | Hongo et al. |
| 2015/0359594 A1 | 12/2015 | Ben-Oren et al. |
| 2015/0359595 A1 | 12/2015 | Ben Oren et al. |
| 2016/0000454 A1 | 1/2016 | Rottenberg et al. |
| 2016/0074196 A1* | 3/2016 | Forsell .................... A61F 2/004 600/31 |
| 2016/0151606 A9 | 6/2016 | Weitzner et al. |
| 2016/0183844 A1 | 6/2016 | Splinter |
| 2016/0184020 A1 | 6/2016 | Kowalewski et al. |
| 2016/0192936 A1 | 7/2016 | Leimbach et al. |
| 2016/0220300 A1 | 8/2016 | Cohen |

FOREIGN PATENT DOCUMENTS

| | | |
|---|---|---|
| EP | 2282803 B1 | 2/2011 |
| WO | 2014118738 A1 | 8/2014 |
| WO | 2014158688 A1 | 10/2014 |
| WO | 2014182946 A2 | 11/2014 |
| WO | 2015089377 A1 | 6/2015 |
| WO | 2015159296 A1 | 10/2015 |
| WO | 2016069754 A1 | 5/2016 |

OTHER PUBLICATIONS

International Preliminary Report on Patentability for International Patent Application No. PCT/US2009/065557, dated Jun. 30, 2011, 6 Pages.
International Search Report and Written Opinion issued in PCT/US2015/057834, dated Jan. 26, 2016, 11 pages.
International Search Report and Written Opinion issued in PCT/US2009/065557 dated Jan. 26, 2010, 12 pages.
Official Action for European Patent Application No. 09833795.9 dated Nov. 20, 2012, 4 pages.

* cited by examiner

LASER ENERGY DELIVERY DEVICES INCLUDING LASER TRANSMISSION DETECTION SYSTEMS AND METHODS

CROSS-REFERENCE TO RELATED APPLICATION

This application is a continuation-in-part of U.S. application Ser. No. 14/925,348, filed Oct. 28, 2015, entitled LASER ENERGY DELIVERY DEVICES INCLUDING LASER TRANSMISSION DETECTION SYSTEMS AND METHODS, which claims the benefit of and priority to, under 35 U.S.C. § 119(e), U.S. Provisional Application Ser. No. 62/072,323, filed Oct. 29, 2014, entitled LASER ENERGY DELIVERY DEVICES INCLUDING LASER TRANSMISSION DETECTION SYSTEMS AND METHODS, and U.S. Provisional Application Ser. No. 62/199,431, filed Jul. 31, 2015, entitled LASER ENERGY DELIVERY DEVICES INCLUDING LASER TRANSMISSION DETECTION SYSTEMS AND METHODS. Each of the above mentioned applications are hereby incorporated by reference in their entireties for all that they teach and for all purposes.

FIELD

The present disclosure relates generally to devices, methods and systems for controlling a laser energy delivery device, and more specifically, to devices, methods, and systems for controlling a laser energy delivery device of a laser ablation system for use in ablating tissue.

BACKGROUND

Arteries are the primary blood vessels that are responsible for providing blood and oxygen to muscles throughout the body. Arterial disease occurs when arteries become narrowed or blocked by a buildup of plaque (for example, atherosclerotic plaque or other deposits). A severe blockage of a peripheral artery may cause non-healing ulcers on the legs and feet, walking pain, rest pain, and/or the potential need for amputation. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it to a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), a procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guide wire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

Some previous laser catheters include components that augment the ablation process, such as aspiration components for removing ablated and other undesired materials. However, previous laser catheters typically lack coordination between transmission of laser energy and actuation of the components that augment the ablation process.

SUMMARY

These and other shortcomings are addressed by the various aspects, embodiments, and configurations of the present disclosure.

A laser energy delivery device in accordance with this disclosure for providing treatment to a subject may include a housing; a coupling carried by the housing and adapted to couple to a laser energy generator; a sheath carried by the housing, the sheath comprising a distal end adapted to be disposed in the subject; a plurality of transport members carried by the sheath, the plurality of transport members adapted to receive laser energy at the coupling, transmit laser energy through the sheath, and deliver laser energy to the subject; a controller carried by the housing; a prime mover carried by the housing and adapted to be actuated by the controller; a drive wire carried by the sheath and eccentrically coupled to the distal end of the sheath, the drive wire adapted to be rotatably driven by the prime mover and rotating to eccentrically rotate the distal end of the sheath; and a plurality of visual indicators carried by the housing, wherein the controller is adapted to energize the plurality of visual indicators based on a rotational position of the prime mover relative to the housing.

The laser energy delivery device as described herein above, wherein the controller is adapted to energize at least one of the visual indicators when the rotational position of the prime mover reaches a threshold.

The laser energy delivery device as described herein above, wherein each visual indicator of the plurality of visual indicators corresponds to a portion of a rotational range of the prime mover, and wherein the controller is adapted to energize each visual indicator when the rotational position of the prime mover is within the portion of the rotational range of each visual indicator.

The laser energy delivery device as described herein above, further comprising a sensor adapted to detect transmission of laser energy through at least one of the plurality of transport members.

The laser energy delivery device as described herein above, wherein the sensor is adapted to send a signal in response to detecting transmission of laser energy through the at least one of the plurality of transport members, wherein the controller is adapted to receive the signal from the sensor, and further comprising an ancillary device adapted to augment treatment of the subject via the laser energy delivery device, the controller actuating the ancillary device upon receiving the signal from the sensor.

The laser energy delivery device as described herein above, wherein the ancillary device comprises: the prime mover; and a drive wire eccentrically coupled to the distal end of the sheath and adapted to be rotatably driven by the prime mover, the drive wire rotating to eccentrically rotate the distal end of the sheath.

The laser energy delivery device as described herein above, wherein the at least one of the plurality of transport members extends from a proximal end to a distal end, and the sensor is adapted to detect emission of laser energy at a location on the at least one of the plurality of transport members disposed between the proximal end and the distal end.

The laser energy delivery device as described herein above, wherein the at least one of the plurality of transport members comprises a bend formed between the proximal end and the distal end, and the sensor is adapted to detect emission of laser energy at the bend.

A laser energy delivery device in accordance with this disclosure for providing treatment to a subject may include a coupling adapted to couple to a laser energy generator; a sheath coupled to the coupling, the sheath including a distal end adapted to be disposed in the subject; a plurality of transport members carried by the coupling and the sheath, the plurality of transport members adapted to receive laser energy at the coupling, transmit laser energy through the sheath, and deliver laser energy to the subject; and a sensor adapted to detect transmission of laser energy through at least one of the plurality of transport members.

The laser energy delivery device as described herein above, wherein the sensor is adapted to send a signal in response to detecting transmission of laser energy through the at least one of the plurality of transport members, and further including a controller adapted to receive the signal from the sensor; and an ancillary device adapted to augment treatment of the subject via the laser energy delivery device, the controller actuating the ancillary device upon receiving the signal from the sensor.

The laser energy delivery device as described herein above, wherein the ancillary devices includes a prime mover adapted to be actuated by the controller; and a drive wire eccentrically coupled to the distal end of the sheath and adapted to be rotatably driven by the prime mover, the drive wire rotating to eccentrically rotate the distal end of the sheath.

The laser energy delivery device as described herein above, further including a control panel including an input operatively coupled to the controller, the input being actuatable by a clinician to cause the laser energy delivery device to enter and exit an automatic mode, in the automatic mode the controller actuating the ancillary device upon receiving the signal from the sensor.

The laser energy delivery device as described herein above, wherein the input is a first input, and the control panel further includes a second input operatively coupled to the controller, the second input being actuatable by the clinician to cause the controller to actuate the ancillary device regardless of whether the controller receives the signal from the sensor.

The laser energy delivery device as described herein above, wherein the at least one of the plurality of transport members extends from a proximal end to a distal end, and the sensor is adapted to detect emission of laser energy at a location on the at least one of the plurality of transport members disposed between the proximal end and the distal end.

The laser energy delivery device as described herein above, wherein the at least one of the plurality of transport members includes a bend formed between the proximal end and the distal end, and the sensor is adapted to detect emission of laser energy at the bend.

The laser energy delivery device as described herein above, wherein the sensor includes a photodiode.

A non-transitory tangible computer-readable storage medium having stored thereon instructions which, when executed by a processor, cause the processor to perform a method that may include detecting transmission of laser energy through at least one of a plurality of laser energy transport members of a laser energy delivery device; and sending a signal to actuate an ancillary device of the laser energy delivery device in response to detecting transmission of laser energy through the at least one of the plurality of transport members.

The non-transitory tangible computer-readable storage medium as described herein above, wherein the ancillary device comprises a prime mover and a drive wire adapted to be rotatably driven by the prime mover and eccentrically coupled to a distal end of a sheath of the laser energy delivery device, and wherein sending the signal to actuate the ancillary device in response to detecting transmission of laser energy through the at least one of the plurality of transport members comprises actuating the prime mover to rotate the drive wire and eccentrically rotate the distal end of the sheath.

The non-transitory tangible computer-readable storage medium as described herein above, wherein sending the signal to actuate the prime mover to rotate the drive wire and eccentrically rotate the distal end of the sheath comprises: sending a first signal to actuate the prime mover and rotate the drive wire and eccentrically rotate the distal end of the sheath in a first direction for a plurality of rotations; and sending a second signal to actuate the prime mover and rotate the drive wire and eccentrically rotate the distal end of the sheath in a second direction for a plurality of rotations, the second direction being opposite the first direction.

The non-transitory tangible computer-readable storage medium as described herein above, wherein sending the signal to actuate the prime mover to rotate the drive wire and eccentrically rotate the distal end of the sheath comprises: sending a first signal to actuate the prime mover and rotate the drive wire and eccentrically rotate the distal end of the sheath in a first direction; deactivating the prime mover to inhibit rotation of the drive wire and the distal end of the sheath when the distal end of the sheath reaches a first rotational limit; sending a second signal to actuate the prime mover and rotate the drive wire and eccentrically rotate the distal end of the sheath in a second direction, the second direction being opposite the first direction; and deactivating the prime mover to inhibit rotation of the drive wire and the distal end of the sheath when the distal end of the sheath reaches a second rotational limit.

The non-transitory tangible computer-readable storage medium as described herein above, wherein the method further includes: detecting a rotational position of the distal end of the sheath and determining when the distal end reaches a rotational limit; and deactivating the prime mover to inhibit rotation of the drive wire and the distal end when the distal end reaches the rotational limit.

The non-transitory tangible computer-readable storage medium as described herein above, wherein the method further includes sending a second signal to actuate the prime mover and eccentrically rotate the distal tip of the sheath to a rotational home position.

A method in accordance with this disclosure for treating a subject by using a laser energy delivery device, the laser energy delivery device including a sheath, a plurality of transport members carried by the sheath, a sensor, and an ancillary device, may include positioning a distal end of the sheath within the subject such that the plurality of transport members are positioned within the subject; transmitting laser energy to the subject via the plurality of transport members; detecting transmission of laser energy through at least one of the plurality of transport members by using the sensor; and actuating the ancillary device in response to detecting transmission of laser energy through the at least one of the plurality of transport members.

The method as described herein above, wherein the ancillary device includes a prime mover and a drive wire adapted to be rotatably driven by the prime mover and eccentrically coupled to the distal end of the sheath, and wherein actuating the ancillary device in response to detecting transmission of laser energy through the at least one of the plurality of transport members includes actuating the prime mover to rotate the drive wire and eccentrically rotate the distal end of the sheath.

The method as described herein above, wherein actuating the prime mover to rotate the drive wire and eccentrically rotate the distal end of the sheath includes rotating the drive wire and eccentrically rotating the distal end of the sheath in a first direction for a plurality of rotations; and subsequently rotating the drive wire and eccentrically rotating the distal end of the sheath in a second direction for a plurality of rotations, the second direction being opposite the first direction.

The method as described herein above, wherein transmitting laser energy to the subject via the plurality of transport members includes transmitting laser energy from a proximal end of the plurality of transport members to a distal end of the plurality of transport members, and detecting transmission of laser energy through the at least one of the plurality of transport members includes detecting transmission of laser energy at a location on the at least one of the plurality of transport members disposed between the proximal end and the distal end of the plurality of transport members.

The method as described herein above, wherein detecting transmission of laser energy at the location on the at least one of the plurality of transport members disposed between the proximal end and the distal end includes detecting emission of laser energy from a bend formed on the at least one of the plurality of transport members between the proximal end and the distal end.

The method as described herein above, wherein the sensor includes a photodiode, and detecting transmission of laser energy through the at least one of the plurality of transport members includes using the photodiode to detect laser energy emitted from the at least one of the plurality of transport members.

A method in accordance with this disclosure for treating a subject by using a laser energy delivery device, the laser energy delivery device including a sheath and a plurality of transport members carried by the sheath, may include positioning the sheath within the subject such that a distal end of the plurality of transport members are positioned within the subject; receiving laser energy at a proximal end of the plurality of transport members; transmitting laser energy from the proximal end to the distal end of the plurality of transport members; delivering laser energy from the distal end of the plurality of transport members to the subject; and detecting emission of laser energy from at least one of the plurality of transport members at a location between the proximal end and the distal end of the plurality of transport members.

The method as described herein above, wherein detecting emission of laser energy from the at least one of the plurality of transport members at the location between the proximal end and the distal end of the plurality of transport members includes detecting emission of laser energy from a bend formed on the at least one of the plurality of transport members between the proximal end and the distal end.

The method as described herein above, wherein detecting emission of laser energy from the bend formed on the at least one of the plurality of transport members between the proximal end and the distal end includes using a photodiode to detect laser energy emitted from the at least one of the plurality of transport members.

The method as described herein above, wherein the laser energy delivery device further includes an ancillary device, and further including actuating the ancillary device in response to detecting emission of laser energy from the bend formed on the at least one of the plurality of transport members.

The method as described herein above, wherein the laser energy delivery device further includes a prime mover and a drive wire adapted to be rotatably driven by the prime mover and eccentrically coupled to a distal end of the sheath, and further including actuating the prime mover to rotate the drive wire and eccentrically rotate the distal end of the sheath in response to detecting emission of laser energy from the at least one of the plurality of transport members.

The method as described herein above, wherein actuating the prime mover to rotate the drive wire and eccentrically rotate the distal end of the sheath includes rotating the drive wire and eccentrically rotating the distal end of the sheath in a first direction for a plurality of rotations, and subsequently rotating the drive wire and eccentrically rotating the distal end of the sheath in a second direction for a plurality of rotations, the second direction being opposite the first direction.

A laser energy delivery device in accordance with this disclosure for providing treatment to a subject may include a sheath including a distal end adapted to be disposed in the subject, a plurality of transport members carried by the sheath, the plurality of transport members adapted to receive laser energy, transmit laser energy through the sheath, and deliver laser energy to the subject, a sensor adapted to send a signal in response to detecting transmission of laser energy through at least one of the plurality of transport members, a controller adapted to receive the signal from the sensor, a prime mover adapted to be actuated by the controller, and a drive wire eccentrically coupled to the distal end of the sheath and adapted to be rotatably driven by the prime mover, the drive wire rotating to eccentrically rotate the distal end of the sheath, and wherein the controller actuates the prime mover to rotate the drive wire and eccentrically rotate the distal end of the sheath in response to receiving the signal from the sensor.

The laser energy delivery device as described herein above, wherein the laser energy delivery device is operable in an automatic mode and a manual mode, in the automatic mode the controller actuating the prime mover to rotate the drive wire and eccentrically rotate the distal end of the sheath in response to receiving the signal from the sensor, and in the manual mode the controller actuating the prime mover to rotate the drive wire and eccentrically rotate the distal end of the sheath regardless of whether the controller receives the signal from the sensor.

The laser energy delivery device as described herein above, further including a first input being actuatable by a clinician to place the laser energy delivery device in the automatic mode, a second input being actuatable by the clinician to cause the controller to actuate the prime mover to rotate the drive wire and eccentrically rotate the distal end of the sheath in a first direction regardless of whether the controller receives the signal from the sensor, and a third input being actuatable by the clinician to cause the controller to actuate the prime mover to rotate the drive wire and eccentrically rotate the distal end of the sheath in a second direction regardless of whether the controller receives the signal from the sensor, the second direction being opposite the first direction.

The laser energy delivery device as described herein above, further including a fourth input being actuatable by the clinician to rotate the drive wire and eccentrically rotate the distal tip of the sheath to a rotational home position.

The laser energy delivery device as described herein above, wherein in the automatic mode the controller actuates the prime mover to rotate the drive wire and eccentrically rotate the distal end of the sheath in a first direction for a plurality of rotations, and subsequently rotate the drive wire and eccentrically rotate the distal end of the sheath in a second direction for a plurality of rotations, the second direction being opposite the first direction.

The laser energy delivery device as described herein above, wherein the drive wire rotates and the distal end of the sheath eccentrically rotates in a first direction and a second direction, the second direction being opposite the first direction, the controller is adapted to deactivate the prime mover when the drive wire and the distal end of the sheath rotate in the first direction and reach a first rotational limit, and the controller is adapted to deactivate the prime mover when the drive wire and the distal end of the sheath rotate in the second direction and reach a second rotational limit.

The laser energy delivery device as described herein above, wherein the plurality of transport members include proximal ends adapted to receive laser energy and distal ends adapted to deliver laser energy to the subject, and the sensor detects transmission of laser energy through the at least one of the plurality of transport members at a position between the proximal ends and the distal ends of the plurality of transport members.

A method in accordance with this disclosure for treating a subject by using a laser energy delivery device, the laser energy delivery device comprising a sheath having a distal end, a plurality of transport members carried by the sheath, a prime mover, a drive wire coupled to the prime mover and eccentrically coupled to the distal end of the sheath, a sensor, and a controller operably coupled to the sensor and the prime mover, may include positioning the distal end of the sheath within the subject such that the plurality of transport members are positioned within the subject; transmitting laser energy to the subject via the plurality of transport members; detecting transmission of laser energy through at least one of the plurality of transport members by using the sensor; sending a signal from the sensor to the controller in response to detecting transmission of laser energy through the at least one of the plurality of transport members; and actuating the prime mover, via the controller, to rotate the drive wire and eccentrically rotate the distal end of the sheath in response to the controller receiving the signal from the sensor.

The method as described herein above, further including operating the laser energy delivery device in an automatic mode, including: detecting transmission of laser energy through the at least one of the plurality of transport members by using the sensor; sending the signal from the sensor to the controller in response to detecting transmission of laser energy through the at least one of the plurality of transport members; actuating the prime mover, via the controller, to rotate the drive wire and eccentrically rotate the distal end of the sheath in response to the controller receiving the signal from the sensor; and operating the laser energy delivery device in a manual mode, including: actuating an input of the laser energy delivery device; and actuating the prime mover, via the controller, to rotate the drive wire and eccentrically rotate the distal end of the sheath in response to actuating the input of the laser energy delivery device.

The method as described herein above, wherein the input is a first input, and operating the laser energy delivery device in the manual mode further includes: actuating the first input of the laser energy delivery device; actuating the prime mover, via the controller, to rotate the drive wire and eccentrically rotate the distal end of the sheath in a first direction in response to actuating the first input of the laser energy delivery device; actuating a second input of the laser energy delivery device; and actuating the prime mover, via the controller, to rotate the drive wire and eccentrically rotate the distal end of the sheath in a second direction in response to actuating the second input of the laser energy delivery device, the second direction being opposite the first direction.

The method as described herein above, wherein operating the laser energy delivery device in the manual mode further includes deactivating the prime mover, via the controller, to inhibit rotation of the drive wire and the distal end of the sheath when the distal end of the sheath reaches a rotational limit.

The method as described herein above, wherein actuating the prime mover includes actuating the prime mover, via the controller, to rotate the drive wire and eccentrically rotate the distal end of the sheath in a first direction in response to the controller receiving the signal from the sensor, and further including: deactivating the prime mover, via the controller, to inhibit rotation of the drive wire and the distal end of the sheath in the first direction when the distal end of the sheath reaches a rotational limit; and actuating the prime mover, via the controller, to rotate the drive wire and eccentrically rotate the distal end of the sheath in a second direction in response to the distal end of the sheath reaching the rotational limit, the second direction being opposite the first direction.

The method as described herein above, wherein the rotational limit is a first rotational limit, and further including: deactivating the prime mover, via the controller, to inhibit rotation of the drive wire and the distal end of the sheath in the second direction when the distal end of the sheath reaches a second rotational limit; and actuating the prime mover, via the controller, to rotate the drive wire and eccentrically rotate the distal end of the sheath in the first direction in response to the distal end of the sheath reaching the second rotational limit.

A laser energy delivery device in accordance with this disclosure for providing treatment to a subject may include a housing, a coupling carried by the housing and adapted to couple to a laser energy generator, a sheath carried by the housing, the sheath including a distal end adapted to be disposed in the subject, a plurality of transport members carried by the sheath, the plurality of transport members adapted to receive laser energy at the coupling, transmit laser energy through the sheath, and deliver laser energy to the subject, a fluid-driven motor carried by the housing and adapted to be driven upon receiving a fluid from a fluid source, and a drive wire carried by the sheath and eccentrically coupled to the distal end of the sheath, the drive wire adapted to be rotatably driven by the fluid-driven motor and rotating to eccentrically rotate the distal end of the sheath.

The laser energy delivery device as described herein above, wherein the fluid-driven motor includes a first inlet/outlet port and a second inlet/outlet port, the fluid-driven motor is adapted to receive the fluid via the first inlet/outlet port and discharge the fluid via the second inlet/outlet port to rotate the fluid-driven motor and the drive wire in a first direction, the fluid-driven motor is adapted to receive the fluid via the second inlet/outlet port and discharge the fluid via the first inlet/outlet port to rotate the fluid-driven motor and the drive wire in a second direction opposite the first direction.

The laser energy delivery device as described herein above, further including a directional control valve coupled to the fluid-driven motor, the directional control valve being adapted to selectively deliver the fluid to the first inlet/outlet port and the second inlet/outlet port of the fluid-driven motor to rotate the drive wire in the first direction and the second direction, respectively.

The laser energy delivery device as described herein above, further including a controller operatively coupled to the directional control valve to selectively deliver the fluid to the first inlet/outlet port and the second inlet/outlet port of the fluid-driven motor to rotate the drive wire in the first direction and the second direction, respectively.

The laser energy delivery device as described herein above, further including a plurality of visual indicators carried by the housing, wherein the controller is adapted to energize the plurality of visual indicators based on a rotational position of the fluid-driven motor relative to the housing.

The laser energy delivery device as described herein above, further including a sensor adapted to detect transmission of laser energy through at least one of the plurality of transport members.

The laser energy delivery device as described herein above, wherein the sensor is adapted to send a signal in response to detecting transmission of laser energy through the at least one of the plurality of transport members, wherein the controller is adapted to receive the signal from the sensor, and further including an ancillary device adapted to augment treatment of the subject via the laser energy delivery device, the controller actuating the ancillary device upon receiving the signal from the sensor.

The laser energy delivery device as described herein above, wherein the ancillary device includes: the fluid-driven motor; and the drive wire.

The laser energy delivery device as described herein above, wherein the directional control valve is a four-way valve.

The laser energy delivery device as described herein above, further including a speed reducer coupling the fluid-driven motor to the drive wire.

The laser energy delivery device as described herein above, wherein the speed reducer is a gearbox.

The laser energy delivery device as described herein above, further including: a controller carried by the housing; and a plurality of visual indicators carried by the housing, wherein the controller is adapted to energize the plurality of visual indicators based on a rotational position of the fluid-driven motor relative to the housing.

The laser energy delivery device as described herein above, wherein the controller is adapted to energize at least one of the visual indicators when the rotational position of the fluid-driven motor reaches a threshold.

The laser energy delivery device as described herein above, wherein each visual indicator of the plurality of visual indicators corresponds to a portion of a rotational range of the fluid-driven motor, and wherein the controller is adapted to energize each visual indicator when the rotational position of the fluid-driven motor is within the portion of the rotational range of each visual indicator.

The laser energy delivery device as described herein above, further including a sensor adapted to detect transmission of laser energy through at least one of the plurality of transport members.

The laser energy delivery device as described herein above, wherein the sensor is adapted to send a signal in response to detecting transmission of laser energy through the at least one of the plurality of transport members, wherein the controller is adapted to receive the signal from the sensor, and further including an ancillary device adapted to augment treatment of the subject via the laser energy delivery device, the controller actuating the ancillary device upon receiving the signal from the sensor.

The laser energy delivery device as described herein above, wherein the ancillary device includes: the fluid-driven motor; and the drive wire.

The laser energy delivery device as described herein above, wherein the at least one of the plurality of transport members extends from a proximal end to a distal end, and the sensor is adapted to detect emission of laser energy at a location on the at least one of the plurality of transport members disposed between the proximal end and the distal end.

The laser energy delivery device as described herein above, wherein the at least one of the plurality of transport members includes a bend formed between the proximal end and the distal end, and the sensor is adapted to detect emission of laser energy at the bend.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1-X_n$, $Y_1-Y_m$, and $Z_1-Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The phrase "fluid power" is the use of fluids, generally under pressure, to generate, control, and transmit power. Fluid power may be generated by a pneumatics power system, which uses a gas such as air (e.g., compressed air) or other gases to generate, control, and transmit power. Fluid power may also be generated by a hydraulic power system, which uses a liquid such as water, saline, and oil (e.g., mineral oil) to generate, control, and transmit power. For example, a fluid-driven motor may convert movement of fluid into mechanical power (energy) and/or electrical power (energy).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

The above and other features of the present disclosure, which alone or in any combination may comprise patentable subject matter, will become apparent from the following description and the attached drawings.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

Figure 1:
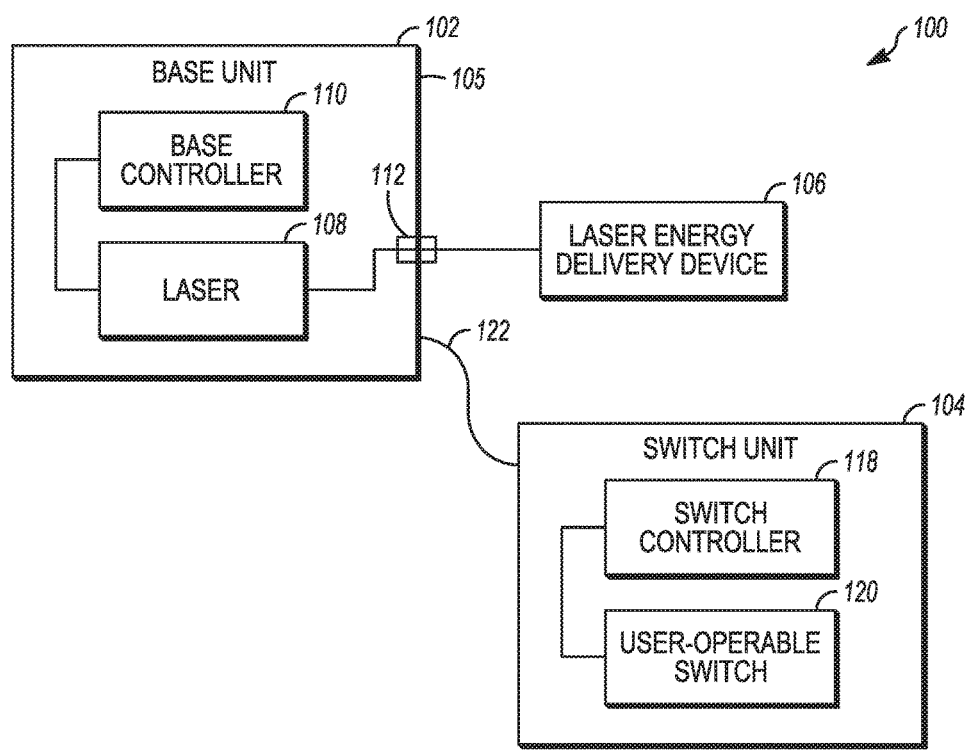
FIG. 1 is a schematic illustration of an exemplary laser ablation system for use in ablating tissue in interventional procedures within the cardiovascular system of a subject.

Corresponding reference characters indicate corresponding parts throughout the several views. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION OF THE DRAWINGS

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to a laser ablation system, it should be understood that the features disclosed herein may have application to other laser ablation systems having a switch unit remote from a base unit.

Figure 2:
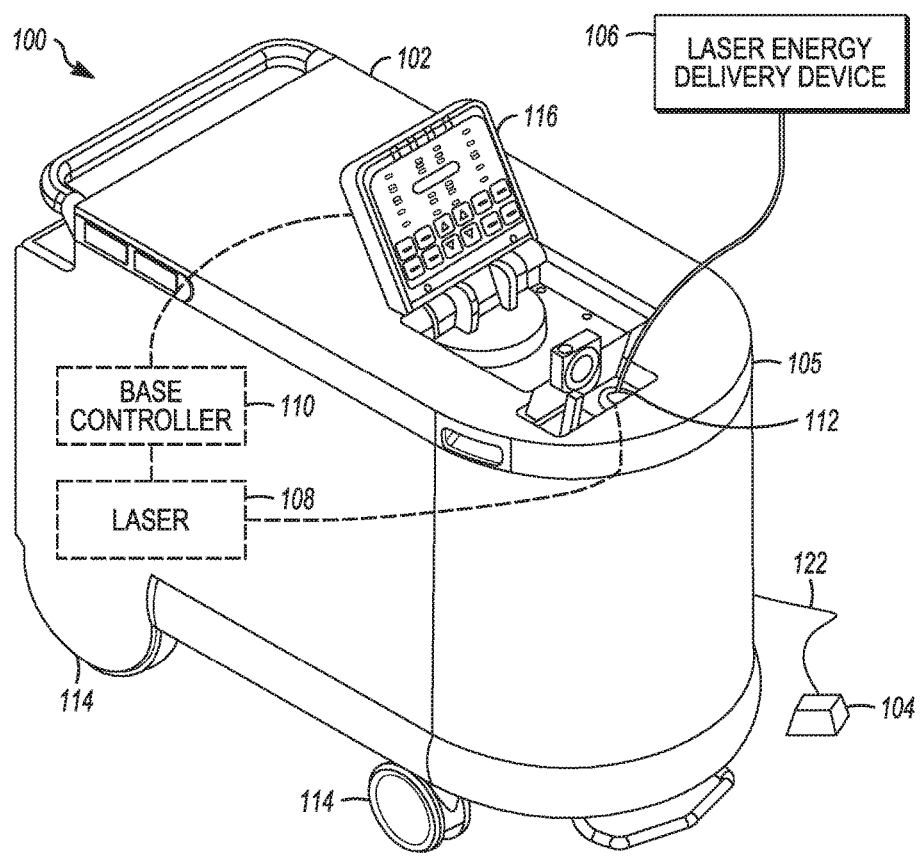
FIG. 2 is another schematic illustration of the laser ablation system of FIG. 1.

FIGS. 1 and 2 illustrate an exemplary laser ablation system 100. The laser ablation system 100 generally includes a laser energy generator or "base unit" 102 that generates laser energy, a switch unit 104 that is operable to actuate the base unit 102, and a laser energy delivery device 106 that delivers laser energy to ablate tissue of a subject.

The base unit 102 includes a housing 105. The housing 105 carries a laser 108 and a base electronic controller 110 that is operatively coupled to the laser 108. The base controller 110 controls operation of the laser 108 and communication of laser energy produced by laser 108 to an output coupling 112 of the base unit 102. As shown in FIG. 2, the housing 105 also carries a plurality of wheels 114 that facilitate movement of the base unit 102. The housing 105 further carries a clinician-operable control panel 116 that is operatively coupled to the base controller 110. The control panel 116 facilitates setting and/or varying operating parameters of the base unit 102.

The base unit 102 may be, for example, the CVX-300 Excimer Laser System available from The Spectranetics Corporation, Colorado Springs, Colo. The base unit 102 may be, for example, as described in U.S. Pat. No. 5,383,199, the entire disclosure of which is expressly incorporated by reference herein for all purposes.

The switch unit 104 includes a switch electronic controller 118 and a clinician-operable switch 120. The clinician-operable switch 120 receives an input from a clinician. Exemplary clinician-operable switches include toggle switches, foot-operated pedal switches, rotary switches, input switches, and other devices via which a clinician can provide an input.

The switch unit 104 is coupled to base unit 102 via a tether 122. A first end of the tether 122 is coupled to the base unit 102 and a second end of the tether 122 is coupled to the switch unit 104. The tether 122 keeps the switch unit 104 within an area surrounding base unit 102 and inhibits the switch unit 104 from being separated from the base unit 102. In some embodiments, the switch unit 104 may be stored within a compartment of the base unit 102 when not in use and positioned remote from the base unit 102 during use of the laser ablation system 100. In these embodiments, the first end of the tether 122 is anchored inside of the storage compartment of the base unit 102. In some embodiments, the tether 122 lacks any power lines and/or communication lines. In these embodiments, the switch unit 104 may include a power supply (not shown) and wirelessly communicate with the base unit 102. In some embodiments, the tether 122 includes one or more power lines and/or communication lines. An exemplary tether is a jacketed, flexible, steel wire safety cable. Other exemplary tethers include ropes, wires, and other flexible members.

Figure 3:
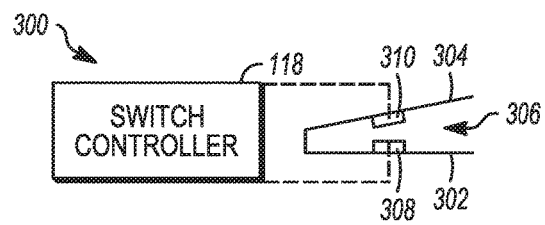
FIG. 3 is a schematic illustration of a clinician-operable foot switch of the laser ablation system of FIG. 1 in an undepressed state.
Figure 4:
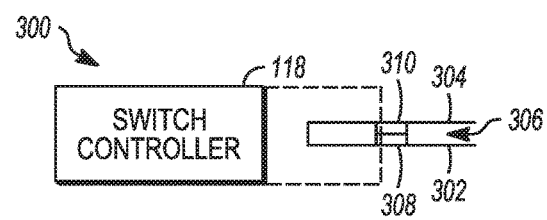
FIG. 4 is a schematic illustration of the clinician-operable foot switch of FIG. 3 in a depressed state.

As described briefly above, the switch unit 104 may be a foot-operated pedal switch. FIGS. 3 and 4 illustrate an exemplary foot-operated pedal switch 300. The pedal switch 300 includes a base 302, a pedal 304 that is moveably coupled to the base 302, and a switch 306 that provides an indication of the position of the pedal 304 relative to the base 302. As shown in FIG. 3, the pedal 304 is rotated upward relative to the base 302. As shown in FIG. 4, the pedal 304 is rotated downward relative to the base 302. In some embodiments, the pedal 304 may be biased to the position shown in FIG. 3 (that is, rotated upward relative to the base 302) by one or more springs (not shown).

The base 302 carries a first contact 308, and the pedal 304 carries a second contact 310. When the contacts 308 and 310 are in contact (see FIG. 4), the pedal switch 300 is in a first state. When the contacts 308 and 310 are spaced apart (see FIG. 3), the pedal switch 300 is in a second state. The switch controller 118 monitors whether the pedal switch 300 is in the first state or the second state. For example, the opening or closing of the pedal switch 300 may change an input voltage to the switch controller 118. A clinician may press down on the pedal 304 to engage the contacts 308 and 310, which causes the switch unit 104 to actuate the base unit 102 and deliver laser energy to the laser energy delivery device 106. In some embodiments, engaging the contacts 308 and 310 causes the base unit 102 to deliver a series of laser energy pulses to the laser energy delivery device 106. The clinician may release the pedal 304 to disengage the contacts 308 and 310, which inhibits the base unit 102 from delivering laser energy to the laser energy delivery device 106.

Figure 5:
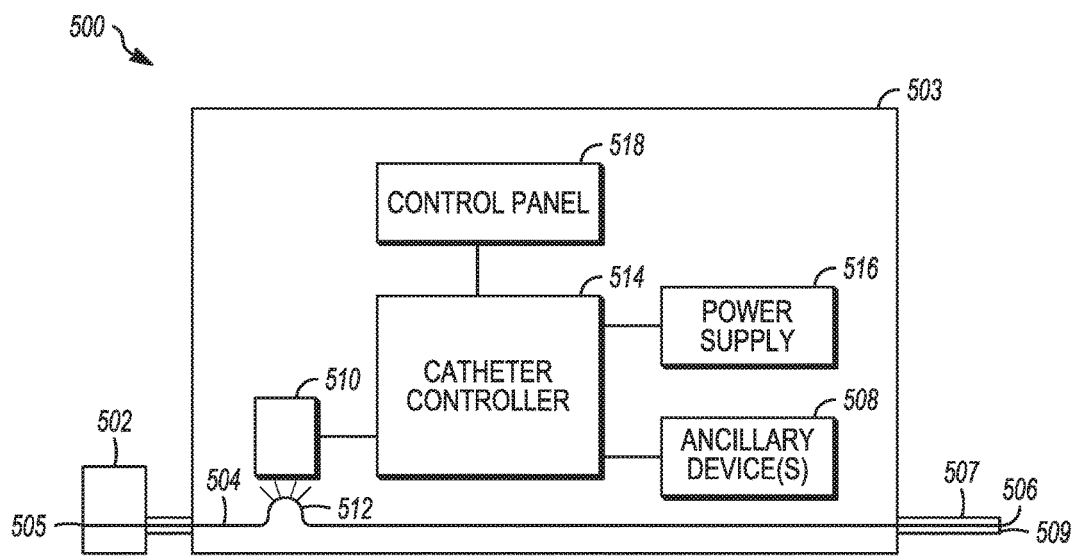
FIG. 5 is a schematic illustration of a laser energy delivery device of the laser ablation system of FIG. 1.

The laser energy delivery device 106 may be a laser ablation catheter. FIG. 5 illustrates an exemplary laser ablation catheter 500. The laser ablation catheter 500 includes an input coupling 502 that couples to the output coupling 112 of the base unit 102. The laser ablation catheter 500 includes one or more transport members 504, such as fiber optic cables. The proximal ends 505 of the transport members 504 are disposed at the input coupling 502 and receive laser energy from the base unit 102. The transport members 504 transmit laser energy from the proximal ends 505, through a housing 503 of the laser ablation catheter 500, and to their distal ends 506, which may be disposed at a distal end 509 of a sheath 507 of the laser ablation catheter 500. When the laser energy reaches the distal ends 506 of the transport members 504, the transport members 504 deliver the laser energy to the environment surrounding the sheath 507 (for example, tissue of the subject).

The laser ablation catheter 500 also includes one or more ancillary devices 508 that augment tissue ablation. The ancillary devices 508 may be carried by the housing 503 and may include, for example, a drive mechanism for translating the laser ablation catheter 500 in the vasculature of the subject, a drive mechanism for rotating the laser ablation catheter 500 in the vasculature of the subject, or an aspiration mechanism for drawing ablated tissue through the laser ablation catheter 500. In some embodiments, the ancillary devices 508 augment tissue ablation by momentarily, instantaneously, and continuously calibrating and adjusting delivered laser energy. In some embodiments, the ancillary devices 508 augment tissue ablation by monitoring the status of the laser ablation catheter 500 and/or the base unit 102. In some embodiments, the ancillary devices 508 may deactivate the laser ablation catheter 500 and/or the base unit 102 upon detecting a malfunction. The laser ablation catheter 500 further includes components for automatically actuating the ancillary device(s) 508 when laser energy is transmitted through the transport members 504. In some embodiments, the laser ablation catheter 500 includes a sensor 510 that is carried by the housing 503. In some embodiments, the sensor 510 includes a photodiode that detects a relatively small amount of laser energy that is emitted, or "leaked", at a curve or bend 512 in one or more of the transport members 504 when laser energy is transmitted through the transport member(s) 504. The sensor 510 may detect various wavelengths or various ranges of wavelengths of emitted laser energy. When the sensor 510 detects emitted laser energy at the bend 512 in the transport member(s) 504, the sensor 510 transmits a signal to a catheter electronic controller 514. In some embodiments, the catheter controller 514 is carried by the housing 503. In some embodiments, the catheter controller 514 is formed by one or more circuits board. Upon receiving the signal from the sensor 510, the catheter controller 514 actuates the ancillary device(s) 508. In some embodiments, the catheter controller 514 delivers energy from a power supply 516, such as a battery, to the ancillary device(s) 508 to actuate the ancillary device(s) 508. In some embodiments, the power supply 516 is carried by the housing 503.

In some embodiments, the catheter controller 514 actuates the ancillary device(s) 508 only when the sensor 510 detects emitted laser energy at the bend 512 (for example, by delivering energy from the power supply 516 to the ancillary device(s) 508). When the sensor 510 does not detect emitted laser energy at the bend 512, the catheter controller 514 deactivates the ancillary device(s) 508 (for example, the catheter controller 514 stops delivering energy from the power supply 516 to the ancillary device(s) 508).

In some embodiments, the catheter controller 514 continuously actuates the ancillary device(s) 508 when the sensor 510 detects a series of emitted laser energy pulses at the bend 512 (for example, by delivering energy from the power supply 516 to the ancillary device(s) 508). When the sensor 510 does not detect emitted laser energy at the bend 512 for a time period that is longer than the time period between laser energy pulses, the catheter controller 514 deactivates the ancillary device(s) 508 (for example, the catheter controller 514 stops delivering energy from the power supply 516 to the ancillary device(s) 508).

In some embodiments, the catheter controller 514 actuates the ancillary device(s) 508 for a predetermined time period after the sensor 510 detects emitted laser energy at the bend 512 (for example, by delivering energy from the power supply 516 to the ancillary device(s) 508). After the predetermined time period elapses, the catheter controller 514 deactivates the ancillary device(s) 508 (for example, the catheter controller 514 stops delivering energy from the power supply 516 to the ancillary device(s) 508).

The bend 512 formed by the transport member(s) 504 may take a variety of shapes and forms. For example, the bend 512 could be formed as one or more turns, loops, or coils of the transport member(s) 504. In some embodiments, the transport members 504 lack any bends 512 and the sensor 510 detects emitted laser energy along a straight portion of one or more of the transport members 504. In some embodiments, the transport members 504 lack any bends 512 and one or more of the transport members 504 terminate before extending into the sheath 507 of the laser ablation catheter 500. These transport member(s) 504 do not deliver laser energy to ablate tissue of the subject. Instead, these transport member(s) 504 deliver laser energy to the sensor 510 to facilitate actuation of the ancillary device(s) 508.

In some embodiments, the portion of the transport member(s) 504 that emits laser energy toward the sensor 510 includes a buffer, coating, sheath, sticker, or patch that facilitates indirect detection of emitted laser energy by the sensor 510. For example, the transport member(s) 504 may include a coating that fluoresces when exposed to laser energy, and the sensor 510 may detect emission of photons by the coating. In some embodiments, the transport member(s) 504 include a fluorophore that is excited by 308 nm laser light, such as coumarin-3-carboxy-(2,2,6,6-tetramethylpiperidine-4-yl)amide[1], and the sensor 510 detects photon emission from the excited fluorophore. In some embodiments, the coatings described above may be combined with other types of coatings for the transport members 504, such as a polyimide coating. In some embodiments, the coatings described above may be present at locations on the transport member(s) 504 where other coatings, such as polyamides, are absent. For example, the coatings may be present on portions of the transport member(s) 504 within the input coupling 502, and the sensor 510 may be carried in the input coupling 502.

Figure 6:
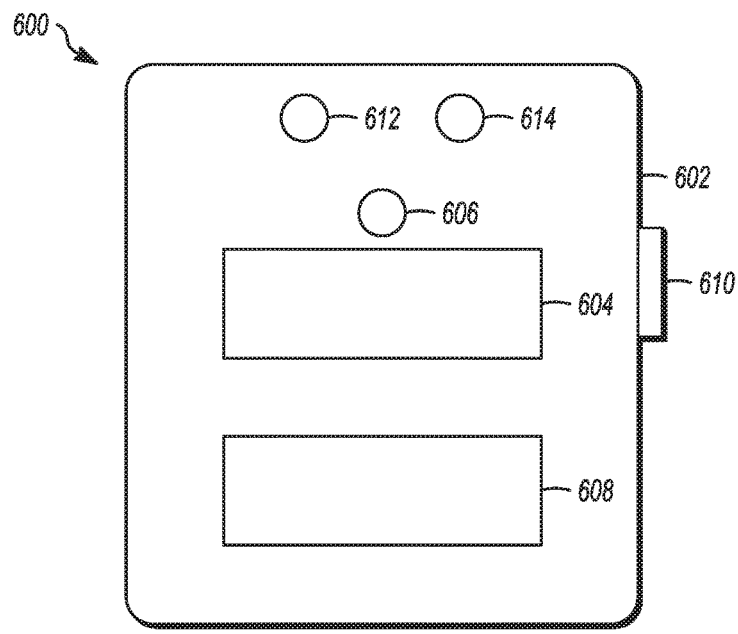
FIG. 6 is an illustration of an exemplary control panel of the laser energy delivery device of FIG. 5.

In some embodiments, the laser ablation catheter 500 includes a control panel 518 that facilitates clinician control of the laser ablation catheter 500. In some embodiments, the control panel 518 is formed on the housing 503. FIG. 6 illustrates an exemplary control panel 600 that may be used as the control panel 518. The control panel 600 includes a housing 602, which may be the housing 503 described above. In some embodiments, the housing 602 carries one or more clinician-operable inputs and/or one or more indicators that are operatively coupled to the catheter controller 514. In some embodiments, the control panel 600 includes a first input 604 (for example, a button) that may be actuated by the clinician to cause the laser ablation catheter 500 to enter an automatic mode. In the automatic mode, the catheter controller 514 automatically controls actuation of the ancillary device(s) 508, for example, in one of the manners described above (that is, the catheter controller 514 actuates the ancillary device(s) 508 when the sensor 510 detects laser energy emitted from the transport member(s) 504). In some embodiments and when the laser ablation catheter 500 is in the automatic mode, the first input 604 may be actuated by the clinician to cause the laser ablation catheter 500 to exit the automatic mode. In some embodiments, the control panel 600 includes a first indicator 606 that indicates when the laser ablation catheter 500 is in the automatic mode. The first indicator 606 may be a visual indicator (for example, a light-emitting diode), an audible indicator (for example, a speaker that emits sound), a tactile indicator (for example, an actuator that facilitates vibration of the control panel 600), or the like.

In some embodiments, the control panel 600 includes a second input 608 (for example, a button) that may be actuated by the clinician to manually actuate the ancillary device(s) 508. That is, the clinician may press the second input 608 to cause the catheter controller 514 to actuate the ancillary device(s) 508 regardless of whether the sensor 510 detects laser energy emitted from the transport member(s) 504.

In some embodiments, the control panel 600 includes a third input 610 (for example, a button) that may be actuated by the clinician to cause the laser ablation catheter 500 to turn "on" and "off". When the laser ablation catheter 500 is "on", the first and second inputs 604 and 608 may be actuated to cause the catheter controller 514 to actuate the ancillary device(s) 508 as described above. When the laser ablation catheter 500 is "off", the catheter controller 514 does not actuate the ancillary device(s) 508 when the first or second inputs 604 and 608 are actuated. In some embodiments, the control panel 600 includes a second indicator 612 that indicates when the laser ablation catheter 500 is "on". The second indicator 612 may be a visual indicator (for example, a light-emitting diode), an audible indicator (for example, a speaker that emit sounds), a tactile indicator (for example, an actuator that facilitates vibration of the control panel 600), or the like.

In some embodiments, the control panel 600 includes a third indicator 614 that indicates when the sensor 510 detects laser energy emitted from the transport member(s) 504. The third indicator 614 be a visual indicator (for example, a light-emitting diode), an audible indicator (for example, a speaker that emit sounds), a tactile indicator (for example, an actuator that facilitates vibration of the control panel 600), or the like.

In some embodiments, the control panel 600 lacks the inputs and indicators described above and instead includes a touch-sensitive display device (not shown; for example, a touch-sensitive LCD device). The touch-sensitive display device acts as an input device that the clinician may manipulate to cause the laser ablation catheter 500 to enter and exit the automatic mode and manually actuate the ancillary device(s) 508. The touch-sensitive display device also provides visual indications when the laser ablation catheter 500 is in the automatic mode and when the sensor 510 detects laser energy emitted from the transport member(s) 504.

Figure 7:
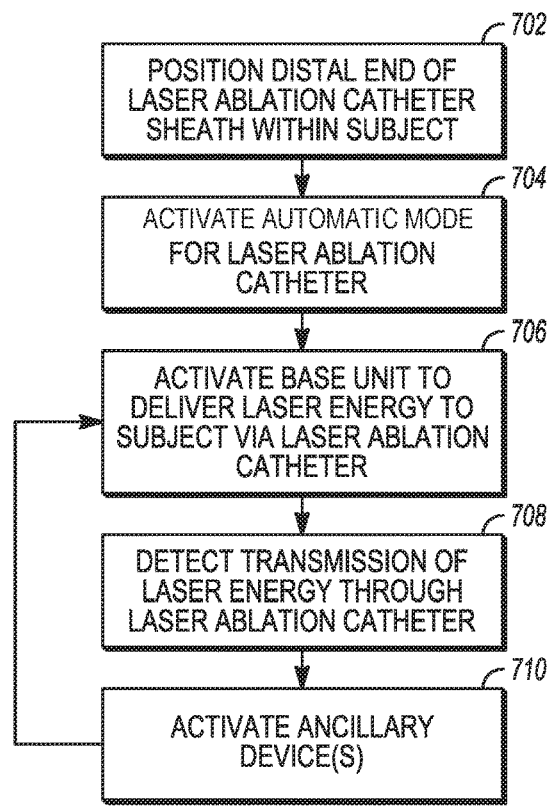
FIG. 7 illustrates an exemplary method for treating a subject by using a laser energy delivery device.

FIG. 7 illustrates an exemplary method for treating a subject by using a laser energy generator and a laser energy delivery device, such as the base unit 102 and the laser ablation catheter 500, respectively. At block 702, the distal end 509 of the laser ablation catheter sheath 507 is positioned within the appropriate tissue of the subject (for example, the vasculature). As a result, the distal ends 506 of the transport members 504 are positioned within the appropriate tissue of the subject. At block 704, the laser ablation catheter 500 is placed in the automatic mode, for example, by pressing the first input 604. At block 706, the base unit 102 is activated to deliver laser energy from the base unit 102, through the laser ablation catheter 500, and to the subject. In some embodiments, for example, the base unit 102 is activated by pressing the foot-operated pedal switch 300. At block 708, the laser ablation catheter 500 detects transmission of laser energy through the transport members 504. In some embodiments, for example, the sensor 510 detects laser energy emitted from the transport members 504 and sends a signal to the catheter controller 514. At block 710, the laser ablation catheter 500 activates the ancillary device(s) 508. In some embodiments, for example, the catheter controller 514 delivers energy from the power supply 516 to actuate the ancillary device(s) 508 upon receiving the signal from the sensor 510. In some embodiments, blocks 706, 708, 710 may occur substantially simultaneously. Blocks 706, 708, and 710 may be repeated any number of times. The distal end 509 of the laser ablation catheter sheath 507 may be translated within the tissue of the subject during blocks 706, 708, and 710.

Figure 8:
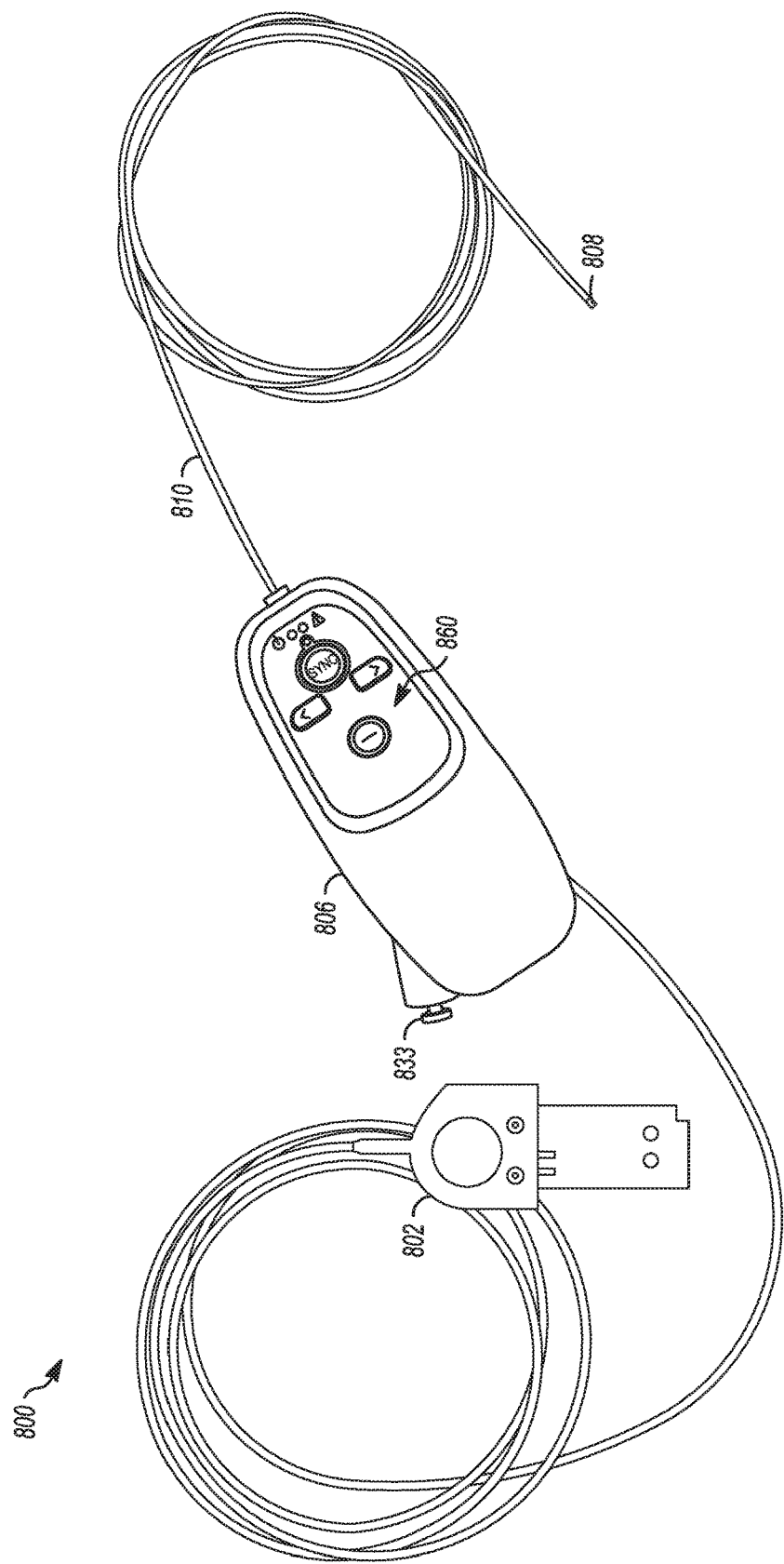
FIG. 8 is an illustration of an exemplary laser ablation catheter.

FIG. 8 illustrates an exemplary laser ablation catheter 800. The laser ablation catheter 800 includes an input coupling 802 that couples to an output coupling of a laser energy generator, such as the output coupling 112 of the base unit 102. The input coupling 802 carries proximal ends of transport members 804 (see FIG. 9) that receive laser energy from the base unit. The transport members 804 transmit laser energy from their proximal ends, through a housing 806 of the laser ablation catheter 800, and to their distal ends, which are disposed at a distal tip or outer band 808 of a sheath 810 of the laser ablation catheter 800. The transport members 804 emit laser energy from their distal ends, or from the distal tip 808, to ablate tissue of the subject.

Generally, the laser ablation catheter 800 includes components that facilitate rotating the distal tip 808 and adjacent portions of the sheath 810 in an "orbital" or "eccentric" manner. The distal tip 808 may rotate in such a manner while delivering laser energy to tissue of a subject to ablate tissue in a circular pattern that is larger than the distal tip 808. The components of the laser ablation catheter 800 also facilitate rotating the distal tip 808 in an automatic mode (that is, rotating the distal tip 808 when laser energy is transmitted through the laser ablation catheter 800) or a manual mode (that is, rotating the distal tip 808 regardless of whether laser energy is transmitted through the laser ablation catheter 800). In some embodiments, the components of the laser ablation catheter 800 inhibit the distal tip 808 from consecutively rotating more than several rotations in one direction to inhibit damaging the transport members 804. These aspects are described in further detail below.

Figure 9:
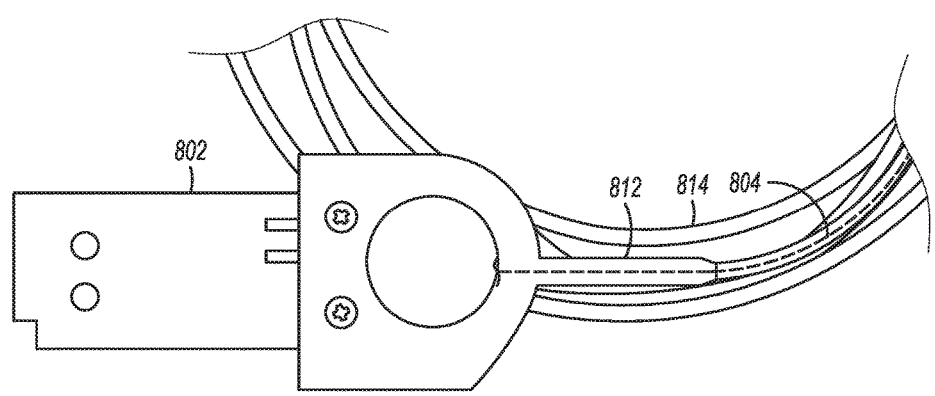
FIG. 9 is an illustration of an input coupling and a partial illustration of a flexible cord of the laser ablation catheter of FIG. 8.

Referring to FIG. 9, in some embodiments, the input coupling 802 is adapted to couple to a laser energy generator, such as the CVX-300 Excimer Laser System available from the Spectranetics Corporation. At the input coupling 802, the laser energy generator delivers laser energy to the proximal ends of the transport members 804 (for example, fiber optic cables). The input coupling 802 may carry various numbers of transport members 804. In some embodiments, the laser ablation catheter includes 106 100 μm fiber optic cables that serve as the transport members 804.

The input coupling 802 couples to a flexible cord 812. In some embodiments, the flexible cord 812 includes a hollow flexible jacket 814 (formed of, for example, a polymer or the like) through which the transport members 804 extend. Opposite the input coupling 802, the flexible cord 812 couples to the housing 806 (see FIG. 10).

Figure 10:
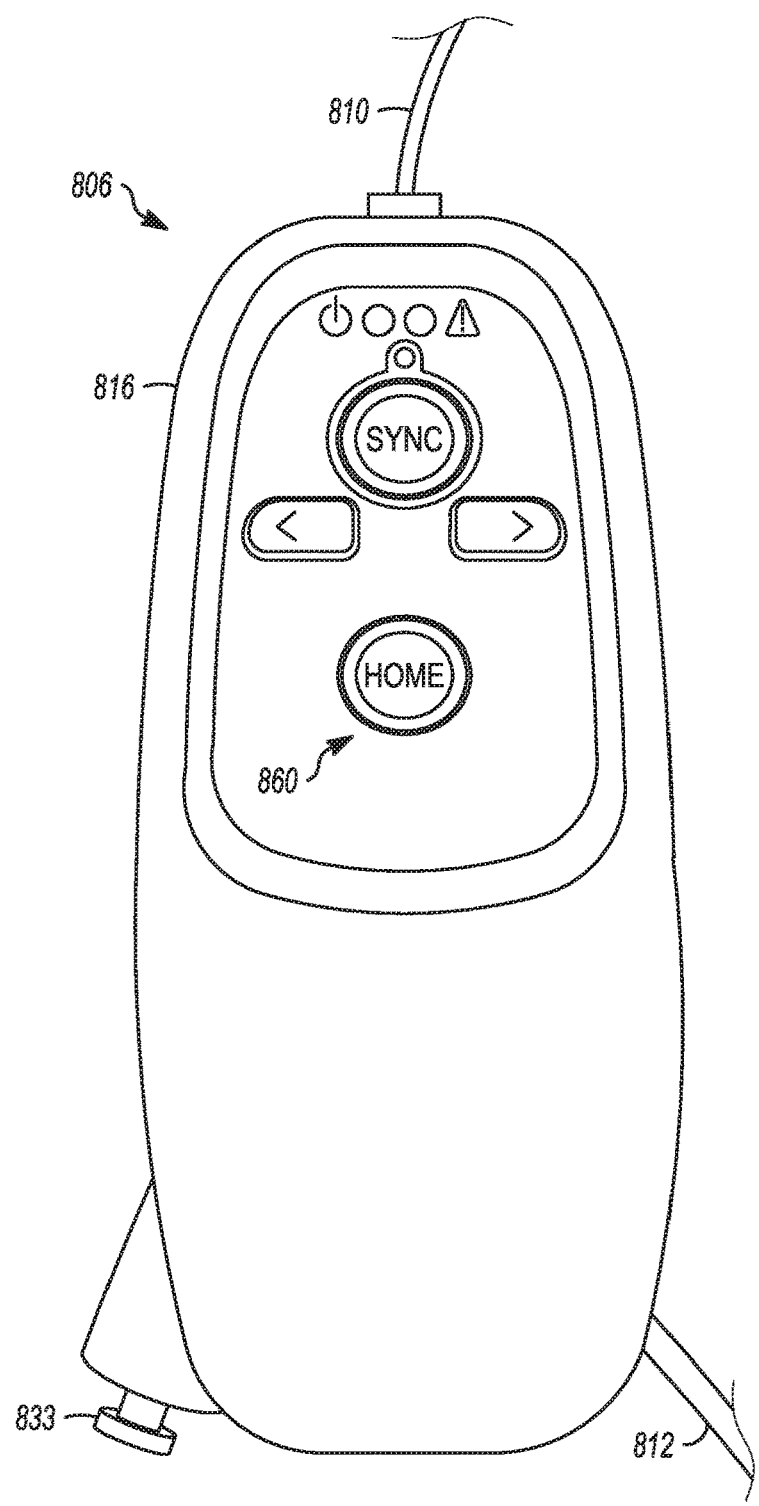
FIG. 10 is an illustration of a housing and a partial illustration of the flexible cord and a laser ablation catheter sheath of the laser ablation catheter of FIG. 8.
Figure 11:
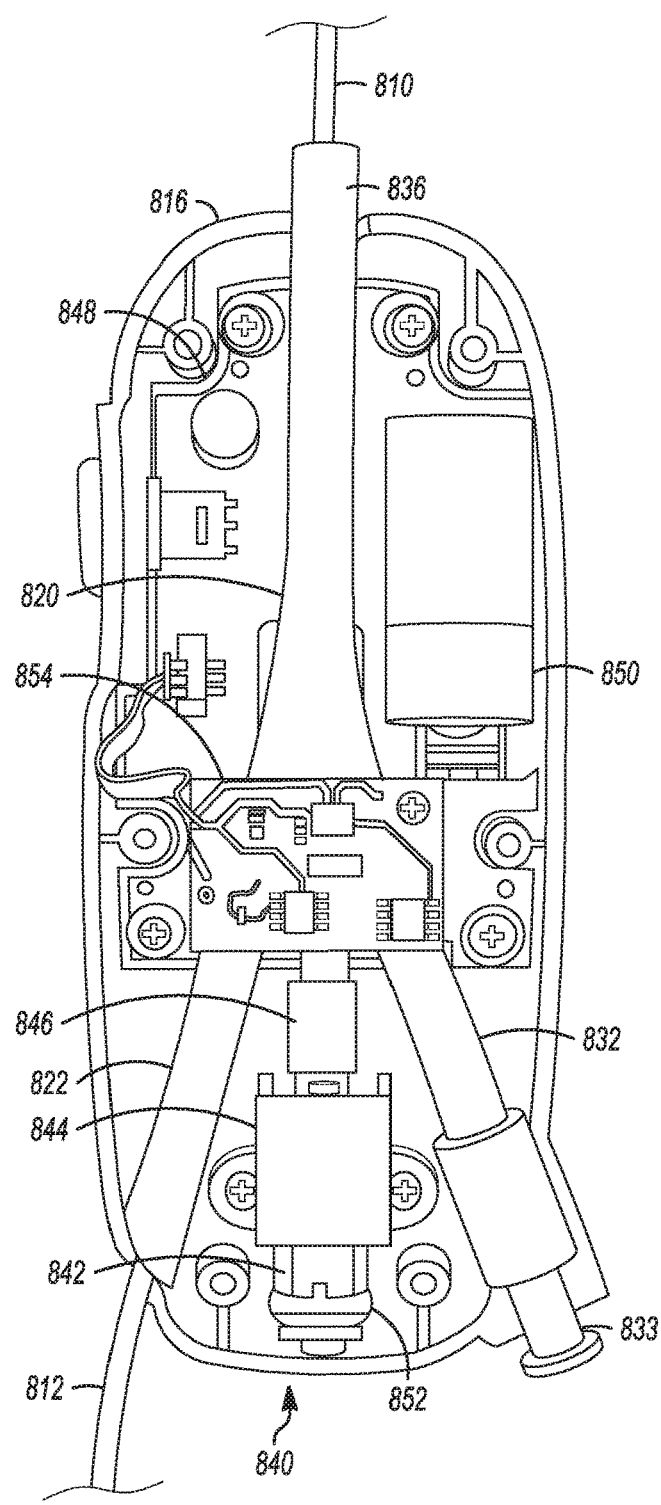
FIG. 11 is an illustration of a base of the housing of FIG. 10 with a cover of the housing removed.
Figure 12:
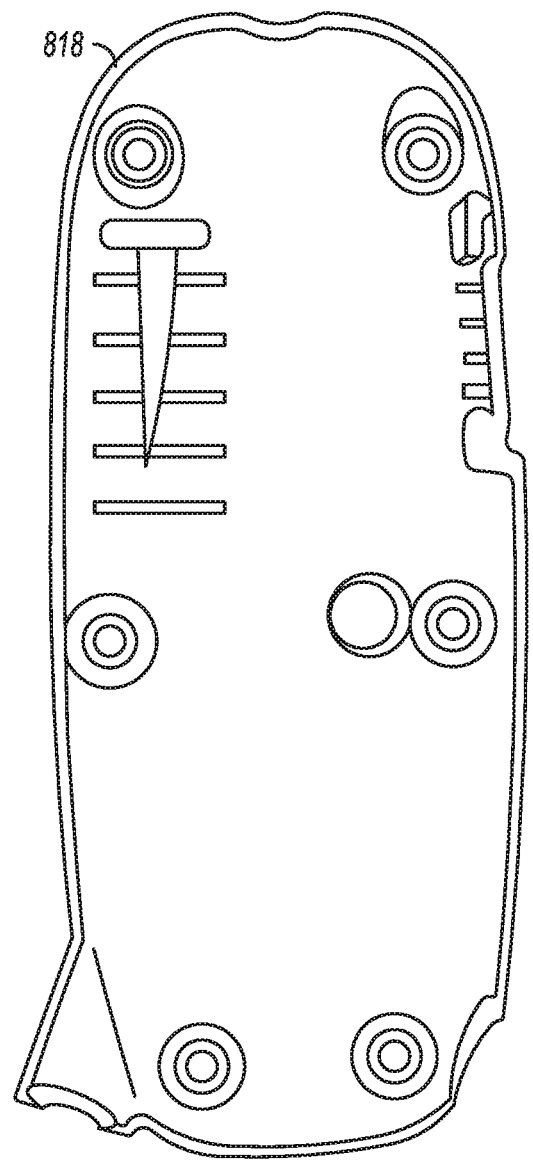
FIG. 12 is an illustration of the cover of the housing of FIG. 10 with the base of the housing removed.

Referring now to FIGS. 10-12, the housing 806 includes a base 816 (see FIGS. 10 and 11) and a cover 818 (see FIG. 12) that may be formed of various materials (for example, a polymer or the like). The base 816 and the cover 818 carry various components. The base 816 and the cover 818 carry a trifurcate structure 820 that joins several components of the laser ablation catheter 800.

Figure 13:
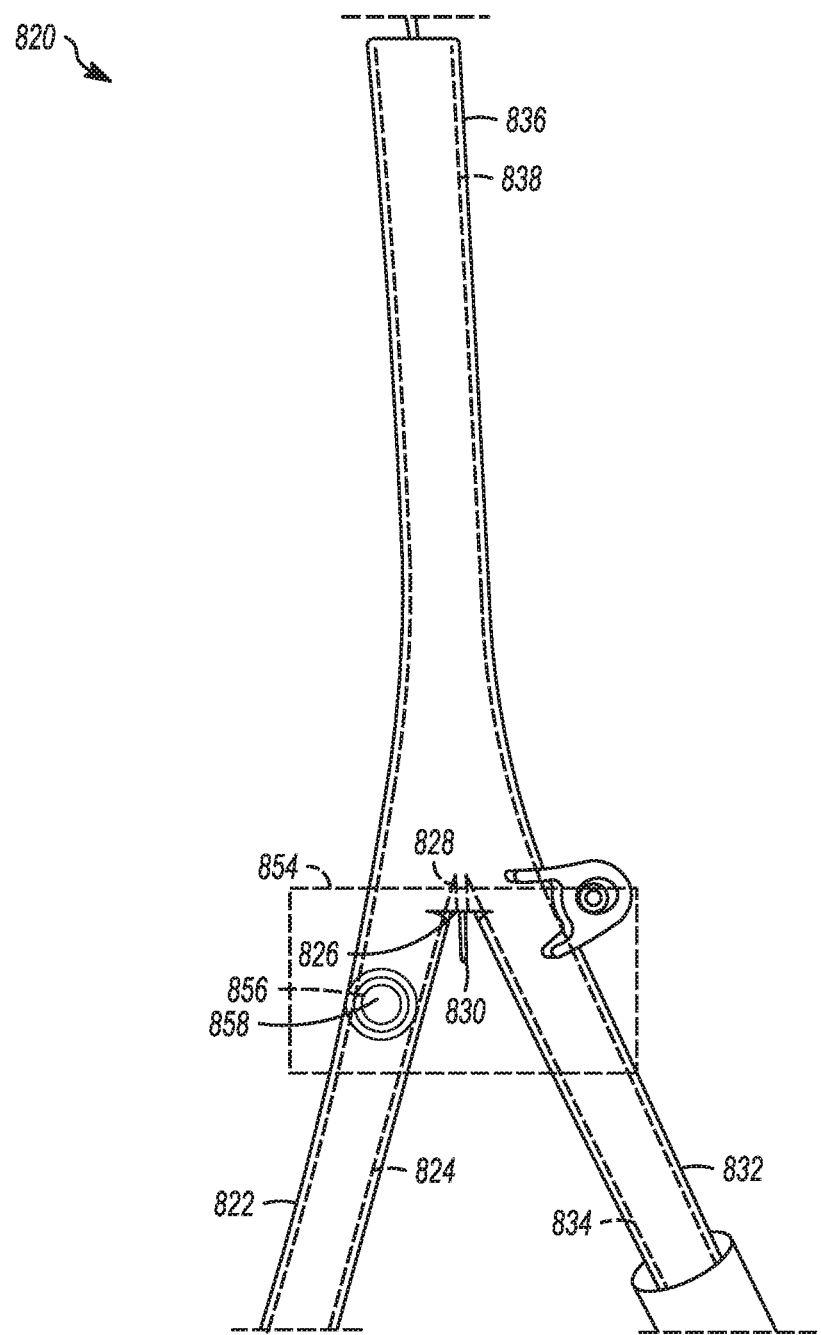
FIG. 13 is a partial illustration of a trifurcate structure of the laser ablation catheter of FIG. 8.
Figure 14:
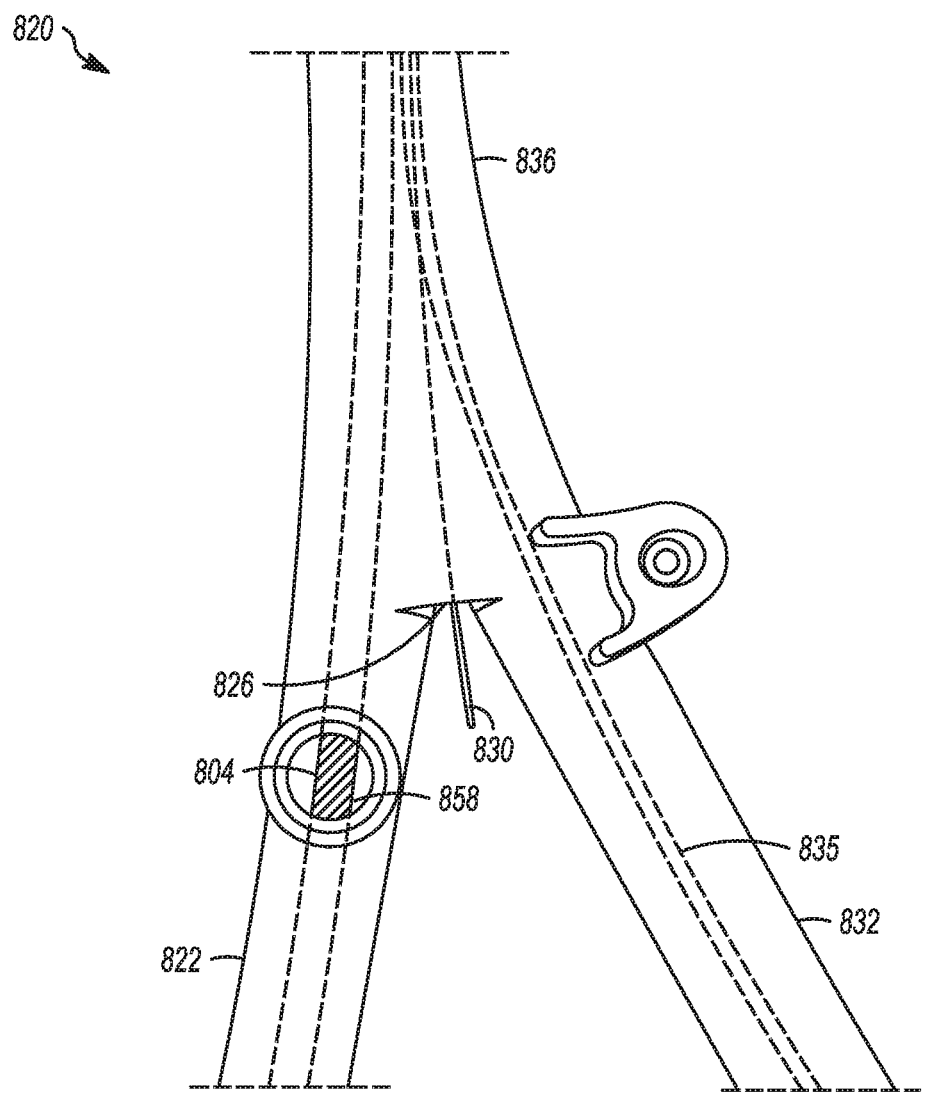
FIG. 14 is another partial illustration of the trifurcate structure of FIG. 13.

The trifurcate structure 820 may be formed of various materials (for example, a polymer or the like). Referring to FIGS. 11, 13, and 14, the trifurcate structure 820 includes a first input branch 822 that defines a first passageway 824 (see FIG. 13). The first input branch 822 couples to the jacket 814 of the flexible cord 812, and the first passageway 824 receives the transport members 804 (see FIG. 14). The trifurcate structure 820 also includes a second input branch 826 that defines a second passageway 828 (see FIG. 13). The second passageway 828 receives a drive or torque wire 830 (see FIG. 13; a flexible wire formed of, for example, stainless steel). As described in further detail below, the drive wire 830 rotates relative to the housing 806 to eccentrically rotate the distal tip 808 of the laser ablation catheter sheath 810. The trifurcate structure 820 further includes a third input branch 832 that defines a third passageway 834 (see FIG. 13). The third input branch 832 couples to a guide wire port 833, such as a Luer connector. The guide wire port 833 in turn couples to a guide wire lumen 835 (for example, via an ultraviolet-cured adhesive; see FIG. 14; the guide wire lumen 835 may be a flexible lumen formed of, for example, stainless steel and adapted to receive, for example, a 0.018 diameter guide wire) that is disposed in the third passageway 834.

In some embodiments, one or more of the input branches 822, 826, and 832 are elongated structures. For example, the first and third input branches 822 and 832 may be elongated structures. In some embodiments, one or more of the input branches 822, 826, and 832 are relatively short structures. For example, the second input branch 826 may be a relatively short structure.

The input branches 822, 826, and 832 couple to an output branch 836, and the input passageways 824, 828, and 834 are in communication with an output passageway 838 (see FIG. 13) defined by the output branch 836. The transport members 804, the drive wire 830, and the guide wire lumen 835 extend from the first passageway 824, the second passageway 828, and the third passageway 834, respectively, and into the output passageway 838. As described in further detail below, the output branch 836 couples to the laser ablation catheter sheath 810 opposite the input branches 822, 826, and 832.

Referring again to FIG. 11, the base 816 and the cover 818 of the housing 806 also carry a prime mover 840 that is coupled to and rotatably drives the drive wire 830. In some embodiments, the prime mover 840 includes an electric motor 842 that drives a speed reducer 844, such as a gearbox. The speed reducer 844 drives a coupling 846 by connecting to the proximal end of the coupling 846, and the coupling 846 drives the drive wire 830. In some embodiments, the distal end of the coupling 846 includes a non-circular opening (for example, a rectangular opening; not shown) that receives a non-circular proximal end of the drive wire 830 (for example, a rectangular proximal end of the drive wire 830). The non-circular opening of the coupling 846 and the non-circular proximal end of the drive wire 830 may be other shapes, such as triangular, trapezoidal, elliptical, or the like. As such, the drive wire 830 may be rotatably fixed to and translatably movable relative to the coupling 846 such that the drive wire 830 may translate relative to the coupling 846 as the drive wire 830 eccentrically rotates the distal tip 808 of the laser ablation catheter sheath 810.

The prime mover 840 and the drive wire 830 together form an ancillary device that augments tissue ablation. Specifically, the prime mover 840 and the drive wire 830 facilitate rotating the distal tip 808 and adjacent portions of the sheath in an eccentric manner.

The housing 806 further carries a catheter electronic controller 848. In some embodiments, the catheter controller 848 is a circuit board. The catheter controller 848 delivers energy from a power supply 850, such as a battery, to the prime mover 840 to drive the prime mover 840, the drive wire 830, and the distal tip 808 of the sheath 810.

In some embodiments, the catheter controller 848 includes a rotational position sensor 852, such as an optical encoder, that is carried by the electric motor 842. The rotational position sensor 852 determines the rotational position of the shaft (not shown) of the electric motor 842. As a result, the rotational position sensor 852 determines the rotational position of the drive wire 830 and the distal tip 808 of the sheath 810. In some embodiments, the catheter controller 848 uses rotational position information to inhibit the distal tip 808 from consecutively rotating more than several rotations in one direction, which in turn inhibits damaging the transport members 804. For example, the catheter controller 848 may limit the rotational range of motion of the distal tip 808 by de-energizing the electric motor 842 when the distal tip 808 reaches a clockwise rotational limit or a counterclockwise rotational limit. When the distal tip 808 is at the clockwise rotational limit, the catheter controller 848 may drive the electric motor 842, and the distal tip 808, in a counterclockwise rotational direction. Similarly, when the distal tip 808 is at the counterclockwise rotational limit, the catheter controller 848 may drive the electric motor 842, and the distal tip 808, in a clockwise rotational direction.

Referring to FIGS. 11 and 13, the housing 806 further carries a laser energy transmission sensor 854. The sensor 854 detects a relatively small amount of laser energy that is emitted, or "leaked", from the transport members 804 when laser energy is transmitted through the transport members 804. In some embodiments, the sensor 854 includes a photodiode 856 (see FIG. 13) that is disposed in an opening 858 formed in the first input branch 822 of the trifurcate structure 820. The opening 858 is in communication with the first passageway 824 of the trifurcate structure 820, and the photodiode 856 is disposed adjacent the transport members 804 to detect laser energy emitted therefrom.

In some embodiments, the sensor 854 detects various wavelengths or various ranges of wavelengths of emitted laser energy. In some embodiments, the sensor 854 detects emitted laser energy having a wavelength of 308 nm.

In some embodiments, the sensor 854 detects emitted laser energy along a straight portion of one or more of the transport members 804. In some embodiments, one or more of the transport members 804 form a curve or bend within the first passageway 824, and the sensor 854 detects laser energy emitted from the bend. The bend may take a variety of shapes and forms. For example, the bend could be formed as one or more turns, loops, or coils in one or more transport members 804.

In some embodiments, the portion of the transport members 804 that emits laser energy toward the sensor 854 includes a buffer, coating, sheath, sticker, or patch that facilitates indirect detection of emitted laser energy by the sensor 854. For example, the transport members 804 may include a coating that fluoresces when exposed to laser energy, and the sensor 854 may detect emission of photons by the coating. In some embodiments, the transport members 804 include a fluorophore that is excited by 308 nm laser light, such as coumarin-3-carboxy-(2,2,6,6-tetramethylpiperidine-4-yl)amide[1], and the sensor 854 detects photon emission from the excited fluorophore. In some embodiments, the coatings described above may be combined with other types of coatings for the transport members 804, such as a polyimide coating.

When the sensor 854 detects laser energy emitted from the transport members 804, the sensor 854 transmits a signal to a catheter controller 848. In some embodiments, upon receiving the signal from the sensor 854, the catheter controller 848 actuates the prime mover 840 to rotate the drive wire 830 and the distal tip 808 of the sheath 810.

In some embodiments, the catheter controller 848 actuates the prime mover 840 (for example, by delivering energy from the power supply 850 to the prime mover 840) only when the sensor 854 detects laser energy emitted from the transport members 804. When the sensor 854 does not detect emitted laser energy, the catheter controller 848 deactivates the prime mover 840 (for example, the catheter controller 848 stops delivering energy from the power supply 850 to the prime mover 840).

In some embodiments, the catheter controller 848 continuously actuates the prime mover 840 (for example, by delivering energy from the power supply 850 to the prime mover 840) when the sensor 854 detects a series of emitted laser energy pulses from the transport members 804. When the sensor 854 does not detect emitted laser energy from the transport members 804 for a time period that is longer than the time period between laser energy pulses, the catheter controller 848 deactivates the prime mover 840 (for example, the catheter controller 848 stops delivering energy from the power supply 850 to the prime mover 840).

In some embodiments, the catheter controller 848 actuates the prime mover 840 for a predetermined time period after the sensor 854 detects laser energy emitted from the transport members 804 (for example, by delivering energy from the power supply 850 to the prime mover 840). After the predetermined time period elapses, the catheter controller 848 deactivates the prime mover 840 (for example, the catheter controller 848 stops delivering energy from the power supply 850 to the prime mover 840).

Figure 15:
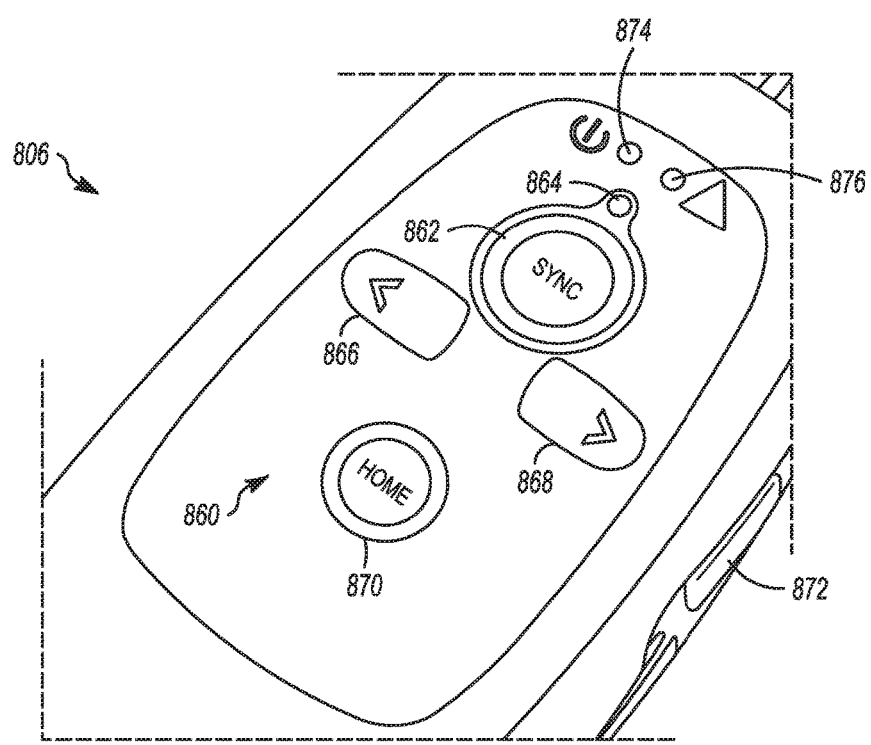
FIG. 15 is an illustration of a control panel of the laser ablation catheter of FIG. 8.
Figure 16:
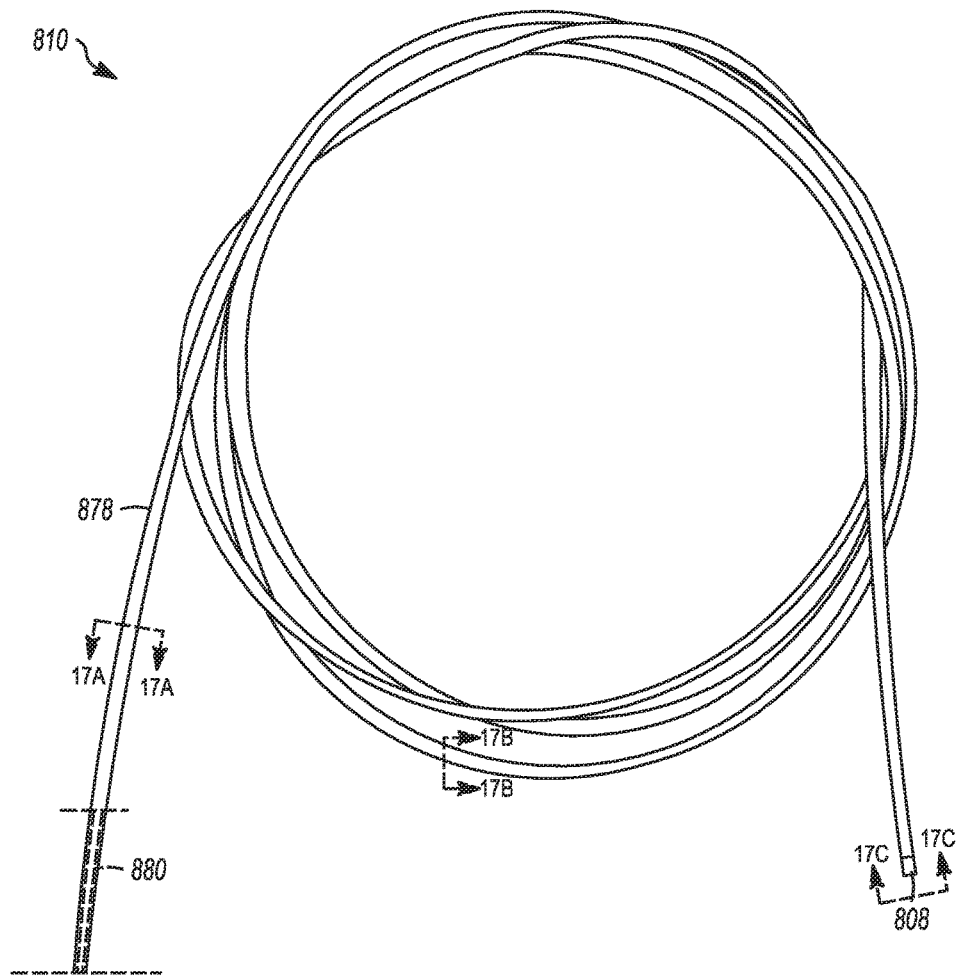
FIG. 16 is a partial illustration of the laser ablation catheter sheath of the laser ablation catheter of FIG. 8.

In some embodiments, the laser ablation catheter 800 includes a control panel 860 (see FIG. 15) that facilitates clinician control of the laser ablation catheter 800. In some embodiments, the control panel 860 is formed on the housing 806. The control panel 860 includes several clinician-operable inputs and/or indicators that are operatively coupled to the catheter controller 848. The control panel 860 includes a first input 862 (for example, a button). The first input 862 may be actuated by the clinician to cause the laser ablation catheter 800 to enter an automatic mode. In the automatic mode, the catheter controller 848 automatically controls actuation of the prime mover 840 and, as a result, rotation of the drive wire 830 and the distal tip 808 of the sheath 810. Specifically, the catheter controller 848 actuates the prime mover 840 only when the sensor 854 detects laser energy is being emitted from the transport members 804. In some embodiments and when the laser ablation catheter 800 is in the automatic mode, the first input 862 may be actuated by the clinician to cause the laser ablation catheter 800 to exit the automatic mode. The control panel 860 includes a first visual indicator 864 (for example, a light-emitting diode) that indicates when the laser ablation catheter 800 is in the automatic mode.

The control panel 860 includes a second input 866 (for example, a button) that may be actuated by the clinician to manually actuate the prime mover 840. That is, the clinician may press the second input 866 to cause the catheter controller 848 to actuate the prime mover 840 regardless of whether the sensor 854 detects laser energy emitted from the transport members 804. In addition, pressing the second input 866 actuates the prime mover 840 in a manner that rotates the drive wire 830 and the distal tip 808 of the sheath 810 in a first direction (for example, clockwise when facing the distal tip 808).

The control panel 860 includes a third input 868 (for example, a button) that may be actuated by the clinician to manually actuate the prime mover 840. That is, the clinician may press the third input 868 to cause the catheter controller 848 to actuate the prime mover 840 regardless of whether the sensor 854 detects laser energy emitted from the transport members 804. In addition, pressing the third input 868 actuates the prime mover 840 in a manner that rotates the drive wire 830 and the distal tip 808 of the sheath 810 in a second direction (for example, counterclockwise when facing the distal tip 808).

In some embodiments, the first input 862 may be actuated by the clinician to cause the laser ablation catheter 800 to enter a "watching" mode. In the watching mode, the catheter controller 848 actuates the prime mover 840 when (1) the sensor 854 detects laser energy is being emitted from the transport members 804 and (2) one of the second input 866 and the third input 868 is actuated (to cause rotation of the distal tip 808 of the sheath 810 in the first and second directions, respectively). In some embodiments and when the laser ablation catheter 800 is in the watching mode, the first input 862 may be actuated by the clinician to cause the laser ablation catheter 800 to exit the watching mode. The first visual indicator 864 may indicate when the laser ablation catheter 800 is in the watching mode.

The control panel 860 includes a fourth input 870 (for example, a button). The fourth input 870 may be actuated by the clinician to actuate the prime mover 840 in a manner that returns the drive wire 830 and the distal tip 808 of the sheath 810 to a rotational "home" position. In some embodiments, the rotational home position is approximately half way between the clockwise rotational limit and the counterclockwise rotational limit. In some embodiments, the catheter controller 848 uses information received from the rotational position sensor 852 to determine a current rotational position of the drive wire 830 and the distal tip 808 of the sheath 810. The catheter controller 848 compares the current rotational position to the rotational home position to determine the direction and amount of rotation needed to return of the drive wire 830 and the distal tip 808 of the sheath 810 to the rotational home position.

In some embodiments, the laser ablation catheter 800 includes a mechanical device (for example, one or more springs) that is adapted to urge the drive wire 830 and the distal tip 808 of the sheath 810 to the rotational home position.

In some embodiments, the control panel 860 includes a fifth input 872 (for example, a button) that may be actuated by the clinician to cause the laser ablation catheter 800 to turn "on" and "off". When the laser ablation catheter 800 is "on", the inputs 862, 866, 868, and 870 may be actuated to cause the catheter controller 848 to actuate the prime mover 840 as described above. When the laser ablation catheter 800 is "off", the catheter controller 848 does not actuate the prime mover 840 when the inputs 862, 866, 868, and 870 are actuated. In some embodiments, the control panel 860 includes a second visual indicator 874 (for example, a light-emitting diode) that indicates when the laser ablation catheter 800 is "on".

In some embodiments, the control panel 860 includes a third visual indicator 876 (for example, a light-emitting diode) that indicates the presence of a device error or fault condition (for example, as detected by the catheter controller 848). For example, device errors and fault conditions may include the prime mover 840 rotating past a rotational limit, a reduction in power to the prime mover 840, and the prime mover 840 failing to rotate in response to actuation of one or more of the inputs 866, 868, and 870.

In some embodiments, when the laser ablation catheter 800 is in the automatic mode and the catheter controller 848 automatically controls actuation of the prime mover 840, the catheter controller 848 monitors the rotational position of the drive wire 830 and the distal tip 808 of the sheath 810 (for example, based on information received from the rotational position sensor 852). When the drive wire 830 and the distal tip 808 of the sheath 810 reach one of the rotational limits, the catheter controller 848 may automatically reverse the direction of rotation of the prime mover 840, the drive wire 830 and the distal tip 808 of the sheath 810. That is, the prime mover 840 may rotate the drive wire 830 and the distal tip 808 of the sheath 810 in a clockwise direction until the drive wire 830 and the distal tip 808 reach the clockwise rotational limit. Thereafter, the prime mover 840 may rotate the drive wire 830 and the distal tip 808 in a counterclockwise direction. Similarly, the prime mover 840 may rotate the drive wire 830 and the distal tip 808 in the counterclockwise direction until the drive wire 830 and the distal tip 808 reach the counterclockwise rotational limit. Thereafter, the prime mover 840 may rotate the drive wire 830 and the distal tip 808 in the clockwise direction. In some embodiments, when the laser ablation catheter 800 is in the automatic mode and the laser energy transmission sensor 854 detects laser energy emitted from the transport members 804, the catheter controller 848 actuates the prime mover 840 in a manner that rotates the distal tip 808 of the sheath 810 in a first direction (for example, a clockwise direction) for several rotations (for example, six rotations), then rotates the distal tip 808 in a second direction (for example, a counterclockwise direction) for several rotations (for example, twelve rotations), then rotates the distal tip 808 in the first direction for several rotations (for example, twelve rotations), and so forth. The distal tip 808 may continue to rotate in this manner until the laser energy transmission sensor 854 no longer detects laser energy emitted from the transport members 804 or for a predetermined number of cycles.

In some embodiments, when the distal tip 808 of the sheath 810 is manually rotated by pressing the inputs 866 and 868, the catheter controller 848 monitors the rotational position of the drive wire 830 and the distal tip 808 (for example, based on information received from the rotational position sensor 852). When the drive wire 830 and the distal tip 808 reach one of the rotational limits, the catheter controller 848 may automatically inhibit rotation of the drive wire 830 and the distal tip 808 (for example, by de-energizing the prime mover 840). That is, the clinician may actuate the second input 866 to rotate the drive wire 830 and the distal tip 808 in a first direction (for example, a clockwise direction) until the drive wire 830 and the distal tip 808 reach a first of the rotational limits (for example, the clockwise rotational limit). The catheter controller 848 then automatically inhibits rotation of the drive wire 830 and the distal tip 808 in the first direction regardless of whether the clinician actuates the second input 866. However, the clinician may actuate the third input 868 to rotate the drive wire 830 and the distal tip 808 in a second direction (for example, a counterclockwise direction). Similarly, the clinician may actuate the third input 868 to rotate the drive wire 830 and the distal tip 808 in the second direction (for example, the counterclockwise direction) until the drive wire 830 and the distal tip 808 reach a second of the rotational limits (for example, the counterclockwise rotational limit). The catheter controller 848 then automatically inhibits rotation of the drive wire 830 and the distal tip 808 in the second direction regardless of whether the clinician actuates the third input 868. However, the clinician may actuate the second input 866 to rotate the drive wire 830 and the distal tip 808 in the first direction (for example, the clockwise direction).

Referring now to FIGS. 16 and 17A-17C, the laser catheter sheath 810 is adapted to be positioned within the vasculature of the subject. The laser catheter sheath 810 includes an outer jacket 878 that is coupled to the output branch 836 of the trifurcate structure 820 (see FIG. 11). The outer jacket 878 is a flexible component that may be formed of, for example, a polymer. The outer jacket 878 defines a sheath passageway 880 that is in communication with the output passageway 838 of the trifurcate structure 820. The sheath passageway 880 receives the transport members 804, the drive wire 830, and the guide wire lumen 835 from the output passageway 880, and the transport members 804, the drive wire 830, and the guide wire lumen 835 extend through the sheath passageway 880 from a proximal end of the sheath 810 to the distal tip 808.

Figure 17A:
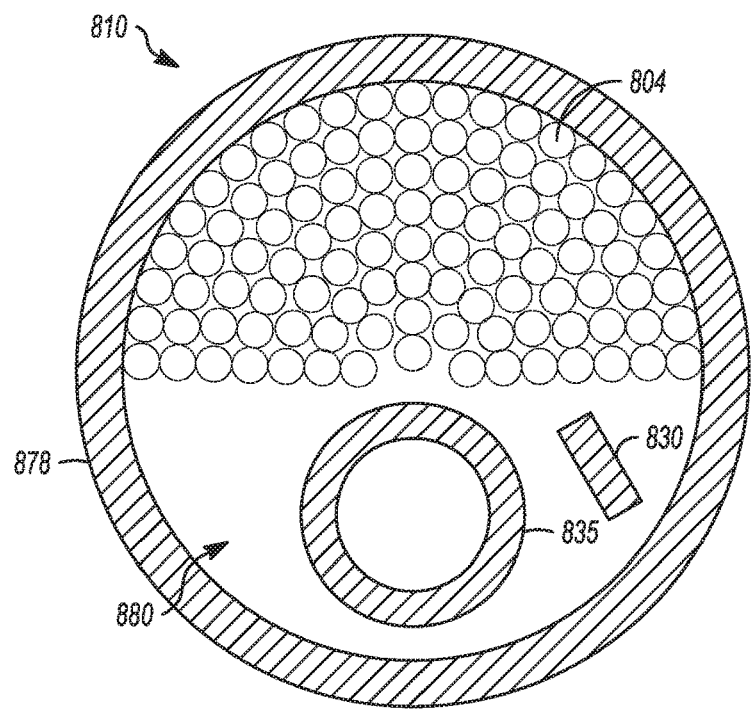
FIG. 17A is a cross-sectional illustration of the laser ablation catheter sheath along line 17A-17A of FIG. 16.

FIG. 17A illustrates a cross-section of a proximal portion of the laser ablation catheter sheath 810. At the proximal portion of the laser ablation catheter sheath 810, the transport members 804, the drive wire 830, and the guide wire lumen 835 are translatably and rotatably disposed within the outer jacket 878. That is, at the proximal portion of the laser ablation catheter sheath 810, the transport members 804, the drive wire 830, the guide wire lumen 835, and the outer jacket 878 are movable relative to each other. In some embodiments, at the proximal portion of the laser ablation catheter sheath 810, the drive wire 830 may have a non-circular cross-sectional shape. For example, the proximal portion of the drive wire 830 may have a rectangular cross-sectional shape including a width of about 0.020 inches and a height of about 0.008 inches. The non-circular cross-sectional shape of the drive wire 830 may extend proximally into the housing 806 and, as described briefly above, couple to a non-circular opening of the prime mover coupling 846. The proximal portion of the drive wire 830 may also have other non-circular cross-sectional shapes, such as triangular, square, pentagonal, hexagonal, octagonal, etc. Additionally or alternatively, the central portion and distal portion of the drive wire 830 may also have such non-circular cross-sectional shapes. For example, the proximal portion of the drive wire 830 may have a circular cross-sectional shape, and the distal portion of the drive wire 830 may have a non-circular cross-sectional shape.

Figure 17B:
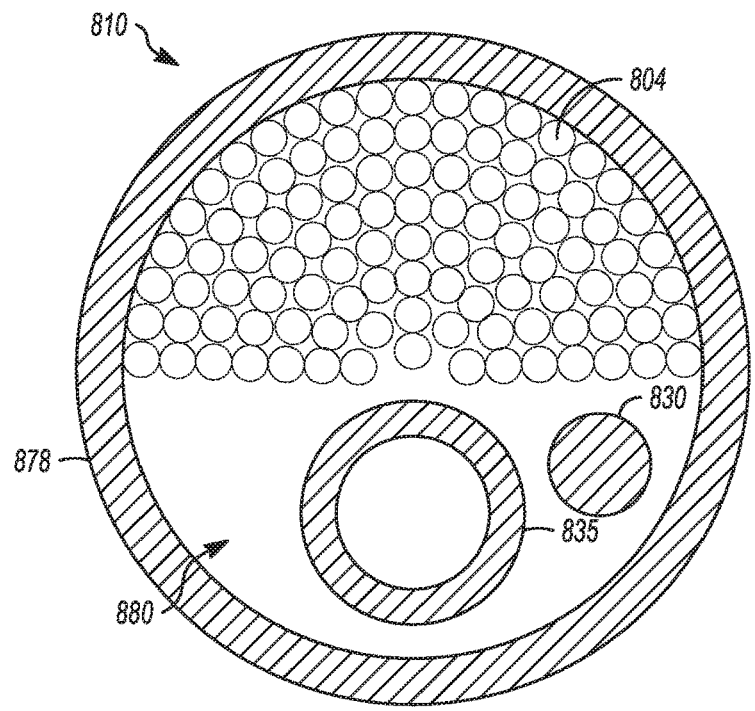
FIG. 17B is a cross-sectional illustration of the laser ablation catheter sheath along line 17B-17B of FIG. 16.

FIG. 17B illustrates a cross-section of an intermediate portion of the laser ablation catheter sheath 810. At the intermediate portion of the laser ablation catheter sheath 810, the transport members 804, the drive wire 830, and the guide wire lumen 835 are translatably and rotatably disposed within the outer jacket 878. That is, at the intermediate portion of the laser ablation catheter sheath 810, the transport members 804, the drive wire 830, the guide wire lumen 835, and the outer jacket 878 are movable relative to each other. In some embodiments, at the intermediate portion of the laser ablation catheter sheath 810, the drive wire 830 may have a circular cross-sectional shape (with a diameter of, for example, 0.014 inches).

Figure 17C:
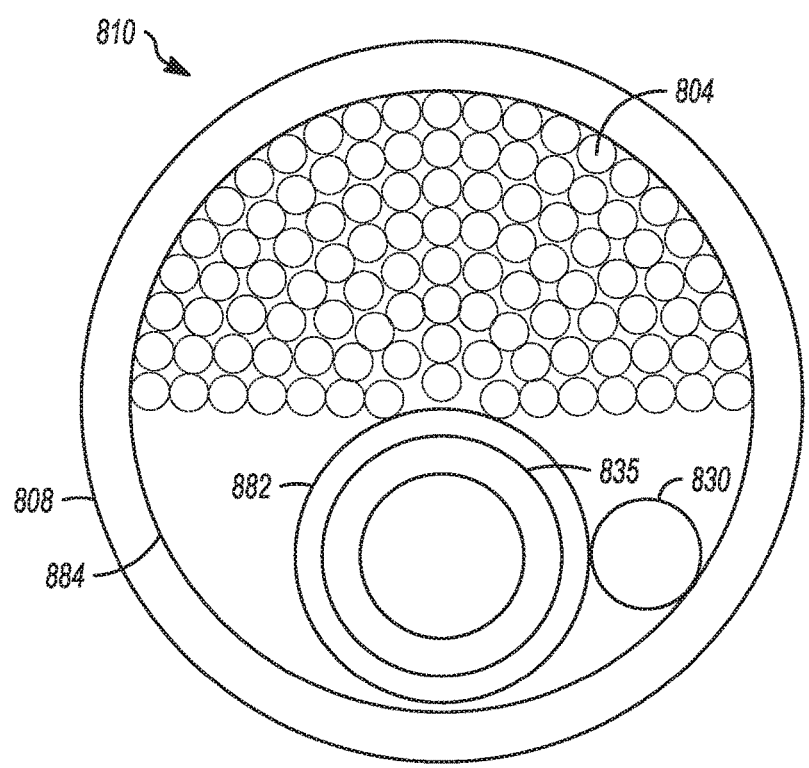
FIG. 17C is an end view illustration of the laser ablation catheter sheath along line 17C-17C of FIG. 16.
Figure 17D:
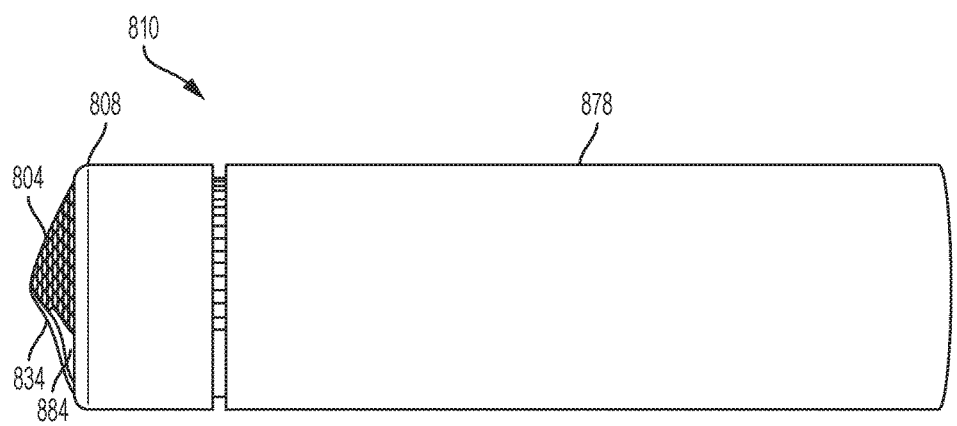
FIG. 17D is a side view illustration of a distal tip of the laser ablation catheter sheath of FIG. 16.

FIGS. 17C and 17D illustrate an end view and a side view, respectively, of the distal tip 808 of the laser ablation catheter sheath 810. In some embodiments, at the distal tip 808, the drive wire 830 may have a circular cross-sectional shape (with a diameter of, for example, 0.021 inches). In some embodiments, the drive wire 830 may have a circular cross-sectional shape that tapers to a smaller diameter proceeding toward the distal tip 808. Such a structure may facilitate deliverability through anatomy. At the distal tip 808, the guide wire lumen 835 is coupled to the drive wire 830 and the distal tip 808 by a first connection 882 (for example, a welded connection). In addition, the first connection 882, the drive wire 830, and the transport members 804 are coupled to each other by a second connection 884 (for example, an epoxy connection). In some embodiments and as shown in FIG. 17D, the transport members 804, the guide wire lumen 835, the drive wire 830, the first connection 882, and the second connection 884 form an atraumatic, conical-shaped leading edge of the distal tip 808. The leading edge may form an angle of about 23 degrees with a plane perpendicular to a longitudinal axis of the laser ablation catheter sheath 810. At the distal tip 808, the guide wire lumen 835 and the drive wire 830 are eccentrically positioned within the distal tip 808. Due to this arrangement, the distal tip 808 rotates in an "orbital" or "eccentric" manner about an eccentric axis when the drive wire 830 rotates. The position of the eccentric axis depends on the stiffness of the drive wire 830 and the stiffness of the guide wire, among other things. In any case, the eccentric rotation of the distal tip 808 permits the transport members 804, which are positioned in a semi-circular array within the distal tip 808, to deliver laser energy and ablate tissue in a circular pattern that is larger than the distal tip 808.

Again, as the prime mover 840 rotates, the drive wire 830 rotates, which in turn causes the distal tip 808 of the sheath 810 to rotate. That is, every rotation of the prime mover 840 creates a corresponding rotation of the drive wire 830. Outside the subject's vasculature and when the sheath 810 is straight, there a one-to-one ratio of rates of rotation between the prime mover 840, the drive wire 830, and the distal tip 808 of the sheath 810. However, when the sheath 810 is placed within a subject's vasculature, which typically includes bends, there is less than a one-to-one ratio of rates of rotation between the (1) prime mover 840 and the proximal end of the drive wire 830 and (2) the distal end of the drive wire 830 and the distal tip 808 of the sheath 810.

In some embodiments, the outer jacket 878, the transport members 804, and the guide wire lumen 835 rotate to a limited extent at the proximal and intermediate portions of the sheath 810 as the drive wire 830 rotates. These components rotate in this manner because they are coupled to the distal tip 808 of the sheath 810.

FIGS. 18A-18E illustrate an exemplary process diagram and method for treating a subject by using a laser energy generator and a laser energy delivery device, such as the base unit 102 and the laser ablation catheter 800, respectively. At block 1802, the distal tip 808 of the laser ablation catheter sheath 810 is positioned within the appropriate tissue of the subject (for example, the vasculature). As a result, the distal ends of the transport members 504 are positioned within the appropriate tissue of the subject. In some embodiments, the catheter sheath 810 is positioned within the appropriate tissue of the subject by inserting the distal end of a guide wire (not shown) into the guide wire port 833. The distal end of the guide wire is translated through the trifurcate structure 820 and the laser ablation catheter sheath 810 such that this distal end of the guide wire protrudes from the distal tip 808 of the laser ablation catheter sheath 810. The guide wire is translated through the vasculature of the subject and crosses a blockage to be ablated. The laser ablation catheter sheath 810 is then translated along the guide wire to position the distal tip 808 near the blockage.

After the distal tip 808 of the laser ablation catheter sheath 810 is positioned within the appropriate tissue of the subject, laser energy may be selectively delivered to the subject (for example, by pressing the foot-operated pedal switch 300).

At block 1804, the catheter controller 848 determines if any of the inputs 862, 866, 868, or 870 have been actuated by the clinician.

Figure 18A:
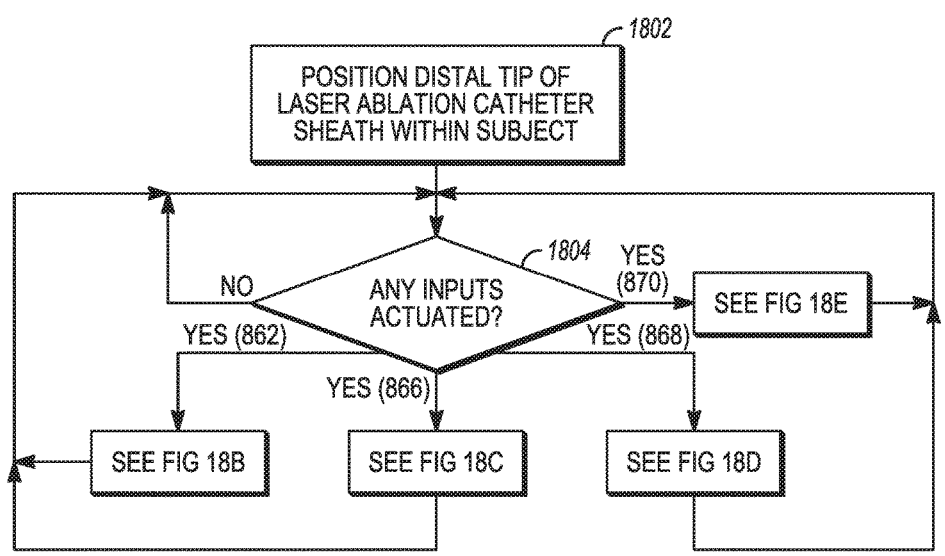
FIGS. 18A-18E illustrate an exemplary process diagram for treating a subject by using a laser energy delivery device.
Figure 18B:
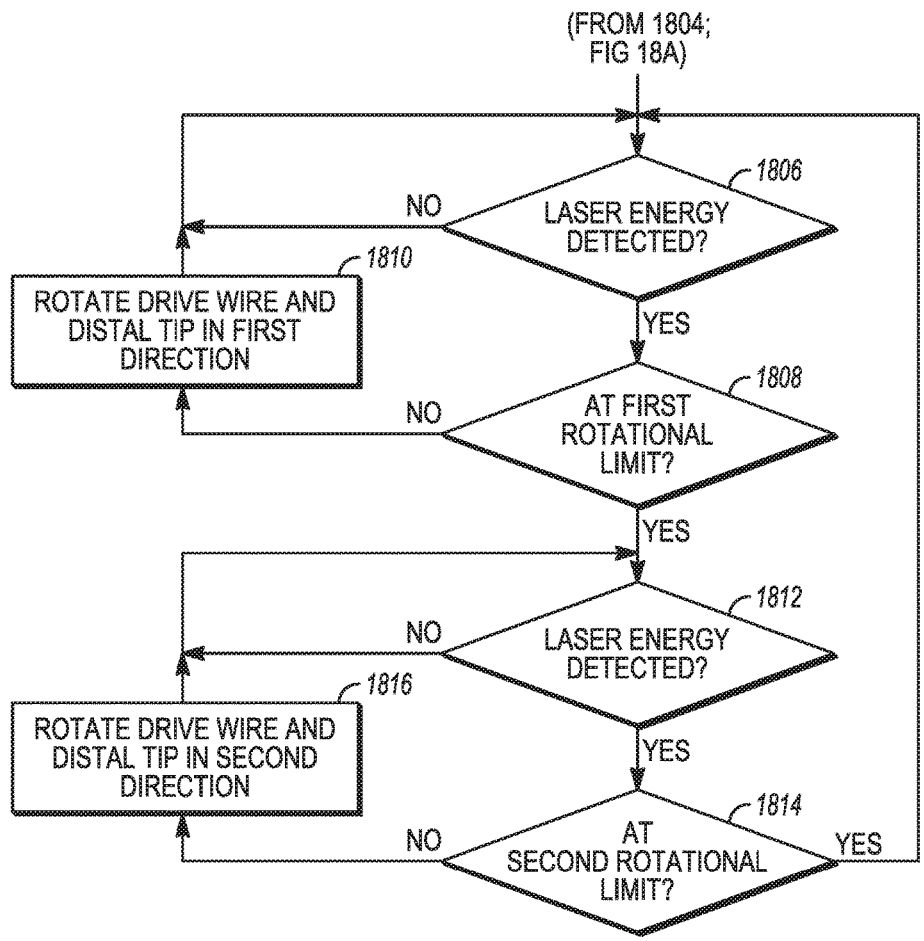

If the first input 862 has been actuated, the laser ablation catheter 800 enters the automatic mode (see FIG. 18B). In the automatic mode, at block 1806, the catheter controller 848 determines if laser energy is being transmitted through the transport members 804 (for example, by receiving the signal from the laser emission energy sensor 854). If laser energy is not being transmitted through the transport members 804, the catheter controller 848 continues to monitor the transport members 804 for laser energy transmission (that is, the catheter controller 848 does not actuate the prime mover 840 to rotate the drive wire 830 and the distal tip 808). If laser energy is being transmitted through the transport members 804, the catheter controller 848 determines if the drive wire 830 and the distal tip 808 are at the first rotational limit (see block 1808; for example, based on information received from the rotational position sensor 852). If the drive wire 830 and the distal tip 808 are not at the first rotational limit, the catheter controller 848 actuates the prime mover 840 to rotate the drive wire 830 and the distal tip 808 in a first direction (see block 1810; for example, a clockwise direction). The catheter controller 848 continues to actuate the prime mover 840 until (1) the drive wire 830 and the distal tip 808 reach the first rotational limit (for example, a clockwise rotational limit), or (2) laser energy is no longer transmitted through the transport members 804 (see block 1806). When the drive wire 830 and the distal tip 808 are at the first rotational limit, the catheter controller 848 does not actuate the prime mover 840 to rotate the drive wire 830 and the distal tip 808 in the first direction, and the process continues to block 1812.

At block 1812, the catheter controller 848 determines if laser energy is being transmitted through the transport members 804 (for example, by receiving the signal from the laser emission energy sensor 854). If laser energy is not being transmitted through the transport members 804, the catheter controller 848 continues to monitor the transport members 804 for laser energy transmission (that is, the catheter controller 848 does not actuate the prime mover 840 to rotate the drive wire 830 and the distal tip 808). If laser energy is being transmitted through the transport members 804, the catheter controller 848 determines if the drive wire 830 and the distal tip 808 are at the second rotational limit (see block 1814; for example, based on information received from the rotational position sensor 852). If the drive wire 830 and the distal tip 808 are not at the second rotational limit, the catheter controller 848 actuates the prime mover 840 to rotate the drive wire 830 and the distal tip 808 in a second direction (see block 1816; for example, a counter-clockwise direction). The catheter controller 848 continues to actuate the prime mover 840 until (1) the drive wire 830 and the distal tip 808 reach the second rotational limit (for example, a counterclockwise rotational limit), or (2) laser energy is no longer transmitted through the transport members 804 (see block 1812). When the drive wire 830 and the distal tip 808 are at the second rotational limit, the catheter controller 848 does not actuate the prime mover 840 to rotate the drive wire 830 and the distal tip 808 in the second direction, and the process returns to block 1806.

The process illustrated in FIG. 18B may continue indefinitely, or the first input 862 may be actuated at any point during the process to exit the automatic mode and return the process to block 1804 (see FIG. 18A).

Figure 18C:
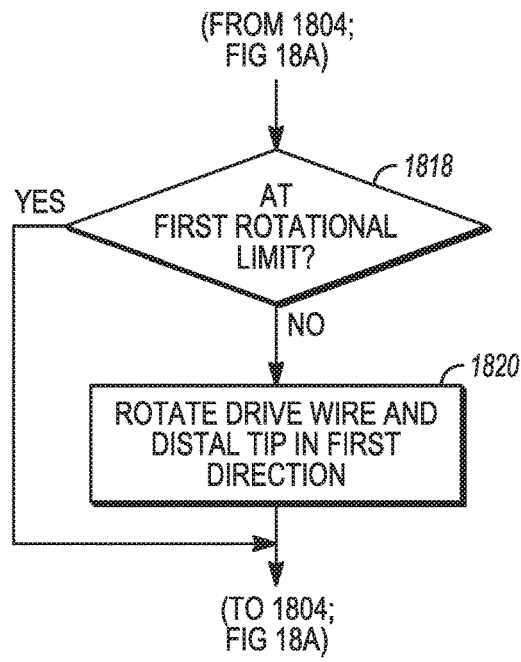

Briefly returning to FIG. 18A, if the second input 866 has been actuated, the laser ablation catheter 800 enters a manual drive mode (see FIG. 18C). At block 1818, the catheter controller 848 determines if the drive wire 830 and the distal tip 808 are at the first rotational limit (for example, based on information received from the rotational position sensor 852). If the drive wire 830 and the distal tip 808 are at the first rotational limit, the process returns to block 1804 (see FIG. 18A; that is, the catheter controller 848 does not actuate the prime mover 840 to rotate the drive wire 830 and the distal tip 808). If the drive wire 830 and the distal tip 808 are not at the first rotational limit, the catheter controller 848 actuates the prime mover 840 to rotate the drive wire 830 and the distal tip 808 in the first direction (see block 1820). The process then returns to block 1804 (see FIG. 18A), although the second input 866 may be continuously actuated (for example, continuously pressed) to continuously rotate the drive wire 830 and the distal tip 808 in the first direction (until reaching the first rotational limit).

Figure 18D:
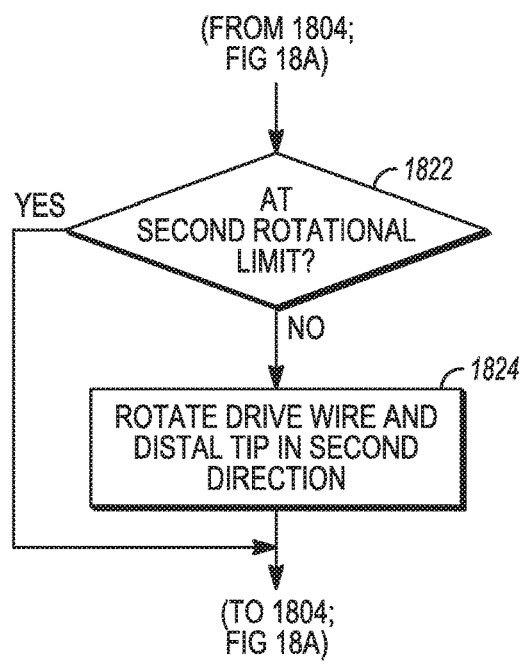

Briefly returning to FIG. 18A, if the third input 868 has been actuated, the laser ablation catheter 800 enters a manual drive mode (see FIG. 18D). At block 1822, the catheter controller 848 determines if the drive wire 830 and the distal tip 808 are at the second rotational limit (for example, based on information received from the rotational position sensor 852). If the drive wire 830 and the distal tip 808 are at the second rotational limit, the process returns to block 1804 (see FIG. 18A; that is, the catheter controller 848 does not actuate the prime mover 840 to rotate the drive wire 830 and the distal tip 808). If the drive wire 830 and the distal tip 808 are not at the second rotational limit, the catheter controller 848 actuates the prime mover 840 to rotate the drive wire 830 and the distal tip 808 in the second direction (see block 1824). The process then returns to block 1804 (see FIG. 18A), although the third input 868 may be continuously actuated (for example, continuously pressed) to continuously rotate the drive wire 830 and the distal tip 808 in the second direction (until reaching the second rotational limit).

Figure 18E:
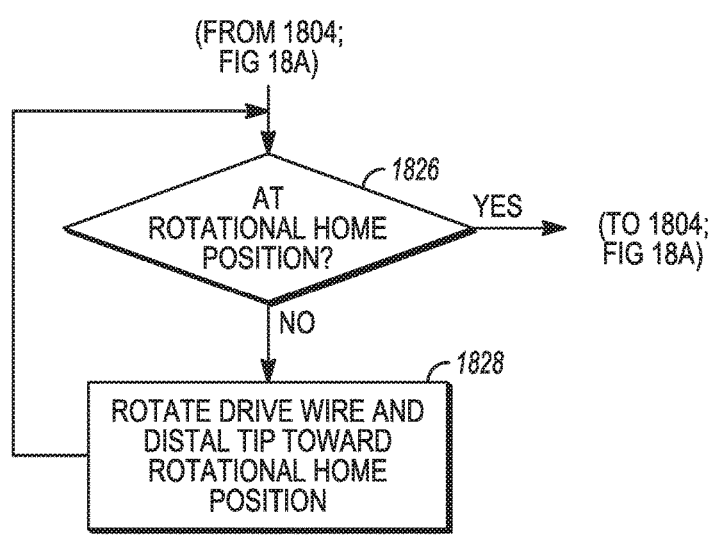

Briefly returning to FIG. 18A, if the fourth input 870 has been actuated, the drive wire 830 and the distal tip 808 return to the rotational home position (see FIG. 18E). At block 1826, the catheter controller 848 determines if the drive wire 830 and the distal tip 808 are at the rotational home position (for example, based on information received from the rotational position sensor 852). If the drive wire 830 and the distal tip 808 are at the rotational home position, the process returns to block 1804 (see FIG. 18A; that is, the catheter controller 848 does not actuate the prime mover 840 to rotate the drive wire 830 and the distal tip 808). If the drive wire 830 and the distal tip 808 are not at the rotational home position, the catheter controller 848 actuates the prime mover 840 to rotate the drive wire 830 and the distal tip 808 toward the rotational home position (see block 1828). The drive wire 830 and the distal tip 808 rotate until they reach the rotational home position, and the process then returns to block 1804 (see FIG. 18A).

In some embodiments, any of the catheter controllers described herein (for example, the catheter controller 514 or 848) may include a non-transitory tangible computer-readable storage medium (for example, flash memory or the like) and a processor. The non-transitory tangible computer-readable storage medium has stored thereon instructions which, when executed by the processor, cause the processor to perform any of the methods or processes described herein (for example, the method illustrated in FIGS. 18A-18E).

Figure 19:
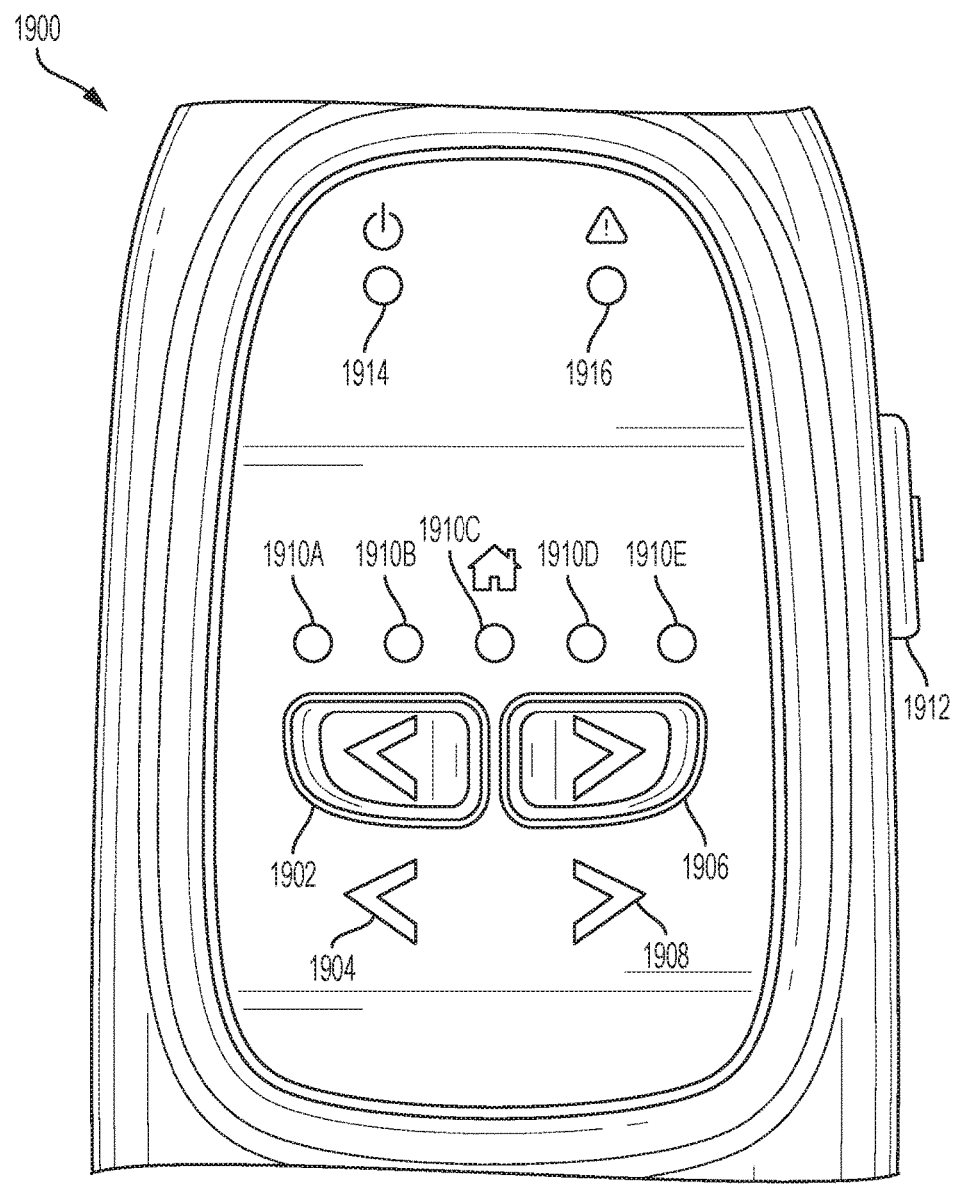
FIG. 19 is an illustration of an exemplary control panel of a laser ablation catheter.

FIG. 19 illustrates an exemplary control panel 1900 of a laser ablation catheter, such as the laser ablation catheter 800 described above. That is, the laser ablation catheter 800 may include the control panel 1900 in lieu of the control panel 860 described above. Components of the laser ablation catheter 800 are referenced in the following description for illustrative purposes, although it is to be understood that the control panel 1900 may be used with other laser ablation catheters.

The control panel 1900 facilitates clinician control of the laser ablation catheter. The control panel 1900 includes several clinician-operable inputs and/or indicators that are operatively coupled to the catheter controller 848.

The control panel 1900 includes a first input 1902 (for example, a button) that may be actuated by the clinician to actuate the prime mover 840. That is, the clinician may press the first input 1902 to cause the catheter controller 848 to actuate the prime mover 840 and thereby rotate the drive wire 830 and the distal tip 808 of the sheath 810. In addition, pressing the first input 1902 actuates the prime mover 840 in a manner that rotates the drive wire 830 and the distal tip 808 of the sheath 810 in a first direction (for example, clockwise when facing the distal tip 808). The control panel 1900 includes a first visual indicator 1904 (for example, a light-emitting diode) that indicates when the first input 1902 is actuated and the prime mover 840, the drive wire 830, and the distal tip 808 of the sheath 810 are rotating in the first direction.

The control panel 1900 includes a second input 1906 (for example, a button) that may be actuated by the clinician to actuate the prime mover 840. That is, the clinician may press the second input 1906 to cause the catheter controller 848 to actuate the prime mover 840 and thereby rotate the drive wire 830 and the distal tip 808 of the sheath 810. In addition, pressing the second input 1906 actuates the prime mover 840 in a manner that rotates the drive wire 830 and the distal tip 808 of the sheath 810 in a second direction (for example, counterclockwise when facing the distal tip 808). The control panel 1900 includes a second visual indicator 1908 (for example, a light-emitting diode) that indicates when the second input 1906 is actuated and the prime mover 840, the drive wire 830, and the distal tip 808 of the sheath 810 are rotating in the second direction.

The control panel 1900 further includes a plurality of visual indicators, such as a third visual indicator 1910A (for example, a light-emitting diode), a fourth visual indicator 1910B (for example, a light-emitting diode), a fifth visual indicator 1910C (for example, a light-emitting diode), a sixth visual indicator 1910D (for example, a light-emitting diode), and a seventh visual indicator 1910E (for example, a light-emitting diode). The visual indicators may be energized (for example, illuminated) based on the rotational position of the prime mover 840 (as determined by the rotational position sensor 852), the proximal end of the drive wire 830, and, generally, the distal end of the drive wire 830 and the distal tip 808 of the sheath 810.

For example, one or more of the visual indicators may be energized when the rotational position of the prime mover 840 reaches or passes a specific threshold, and one of the visual indicators may be energized when the rotational position of the prime mover 840 has not reached a threshold. As a specific example, the prime mover 840 may have a "home" position in which the drive wire 830 and the distal end of the sheath 810 are not rotated relative to the housing 806. From the home position, the prime mover 840 may rotate over an angle $\alpha$ (for example, 2160 degrees) in a first direction (that is, the prime mover 840 may rotate until it reaches a first rotational limit, referred to here as $+\alpha$). The first direction may be, for example, clockwise when facing the distal tip 808. Similarly, from the home position the prime mover 840 may rotate over the angle $\alpha$ in a second direction (that is, the prime mover 840 may rotate until it reaches a second rotational limit, referred to here as $-\alpha$). The second direction may be, for example, counterclockwise when facing the distal tip 808. As such, the rotational range of the prime mover 840 is $2\alpha$ (for example, 4320 degrees). The rotational position of the prime mover 840 is referred to here as $\beta$ and the home position is defined as $\beta=0$. As such, $\beta$ is positive when the rotational position of the prime mover 840 is closer to the first rotational limit than the second rotational limit and $\beta$ is negative when the rotational position of the prime mover 840 is closer to the second rotational limit than the first rotational limit. With this definition, the visual indicator thresholds may be $+\alpha$, $+0.5\alpha$, $-0.5\alpha$, $-\alpha$, and the visual indicators may be energized, as follows:

third visual indicator 1910A: $\beta=+\alpha$
fourth visual indicator 1910B: $+\alpha>\beta\geq+0.5\alpha$
fifth visual indicator 1910C: $+0.5\alpha>\beta>-0.5\alpha$
sixth visual indicator 1910D: $-0.5\alpha\geq\beta-\alpha$
seventh visual indicator 1910E: $\beta=-\alpha$ Stated another way, for example, the third visual indicator 1910A is energized when the rotational position of the prime mover 840 is 2160 degrees (that is, $\beta=2160$ degrees) and the seventh visual indicator 1910E is energized when the rotational position of the prime mover 840 is $-2160$ degrees (that is, $\beta=-2160$ degrees).

As another example, each visual indicator may correspond to a portion of the rotational range of the prime mover 840, and each visual indicator may be energized when the prime mover 840 is rotationally positioned with its specific portion of the rotational range. As a specific example, the prime mover 840 may have a "home" position in which the drive wire 830 and the distal end of the sheath 810 are not rotated relative to the housing 806. From the home position, the prime mover 840 may rotate over an angle α (for example, 2160 degrees) in a first direction (that is, the prime mover 840 may rotate until it reaches a first rotational limit, referred to here as +α). The first direction may be, for example, clockwise when facing the distal tip 808. Similarly, from the home position the prime mover 840 may rotate over the angle α in a second direction (that is, the prime mover 840 may rotate until it reaches a second rotational limit, referred to here as −α). The second direction may be, for example, counterclockwise when facing the distal tip 808. As such, the rotational range of the prime mover 840 is 2α (for example, 4320 degrees). The rotational position of the prime mover 840 is referred to here as β and the home position is defined as β=0. As such, β is positive when the rotational position of the prime mover 840 is closer to the first rotational limit than the second rotational limit and β is negative when the rotational position of the prime mover 840 is closer to the second rotational limit than the first rotational limit. With this definition, the visual indicators may be energized when the rotational position of the prime mover 840 is as follows:

third visual indicator 1910A: $+\alpha \geq \beta > +0.75\alpha$
fourth visual indicator 1910B: $+0.75\alpha \geq \beta > +0.25\alpha$
fifth visual indicator 1910C: $+0.25\alpha \geq \beta \geq -0.25\alpha$
sixth visual indicator 1910D: $-0.25\alpha > \beta \geq -0.75\alpha$
seventh visual indicator 1910E: $-0.75\alpha > \beta \geq -\alpha$ With the previous definition and as another example, the visual indicators may be energized when the rotational position of the prime mover 840 is as follows:

third visual indicator 1910A: $+\alpha \geq \beta \geq +(5/6)\alpha$
fourth visual indicator 1910B: $+(5/6)\alpha > \beta > +(1/6)\alpha$
fifth visual indicator 1910C: $+(1/6)\alpha \geq \beta \geq -(1/6)\alpha$
sixth visual indicator 1910D: $-(1/6)\alpha > \beta > -(5/6)\alpha$
seventh visual indicator 1910E: $-(5/6)\alpha \geq \beta \geq -\alpha$ With the previous definition and as yet another example, the visual indicators may be energized when the rotational position of the prime mover 840 is as follows:

third visual indicator 1910A: $+\alpha \geq \beta \geq +(5/6)\alpha$
fourth visual indicator 1910B: $+(5/6)\alpha > \beta > +(1/3)\alpha$
fifth visual indicator 1910C: $+(1/3)\alpha \geq \beta \geq -(1/3)\alpha$
sixth visual indicator 1910D: $-(1/3)\alpha > \beta > -(5/6)\alpha$
seventh visual indicator 1910E: $-(5/6)\alpha \geq \beta \geq -\alpha$ The control panel 1900 further includes a third input 1912 (for example, a button) that may be actuated by the clinician to cause the laser ablation catheter 800 to turn "on" and "off". When the laser ablation catheter 800 is "on", the inputs 1902 and 1906 may be actuated to cause the catheter controller 848 to actuate the prime mover 840 as described above. When the laser ablation catheter 800 is "off", the catheter controller 848 does not actuate the prime mover 840 when the inputs 1902 and 1906 are actuated. In some embodiments, the control panel 1900 includes an eighth visual indicator 1914 (for example, a light-emitting diode) that indicates when the laser ablation catheter 800 is "on".

In some embodiments, the control panel 1900 includes a ninth visual indicator 1916 (for example, a light-emitting diode) that indicates the presence of a device error or fault condition (for example, as detected by the catheter controller 848). For example, device errors and fault conditions may include the prime mover 840 rotating past a rotational limit, a reduction in power to the prime mover 840, and the prime mover 840 failing to rotate in response to actuation of one or more of the inputs 1902 and 1906.

Figure 20:
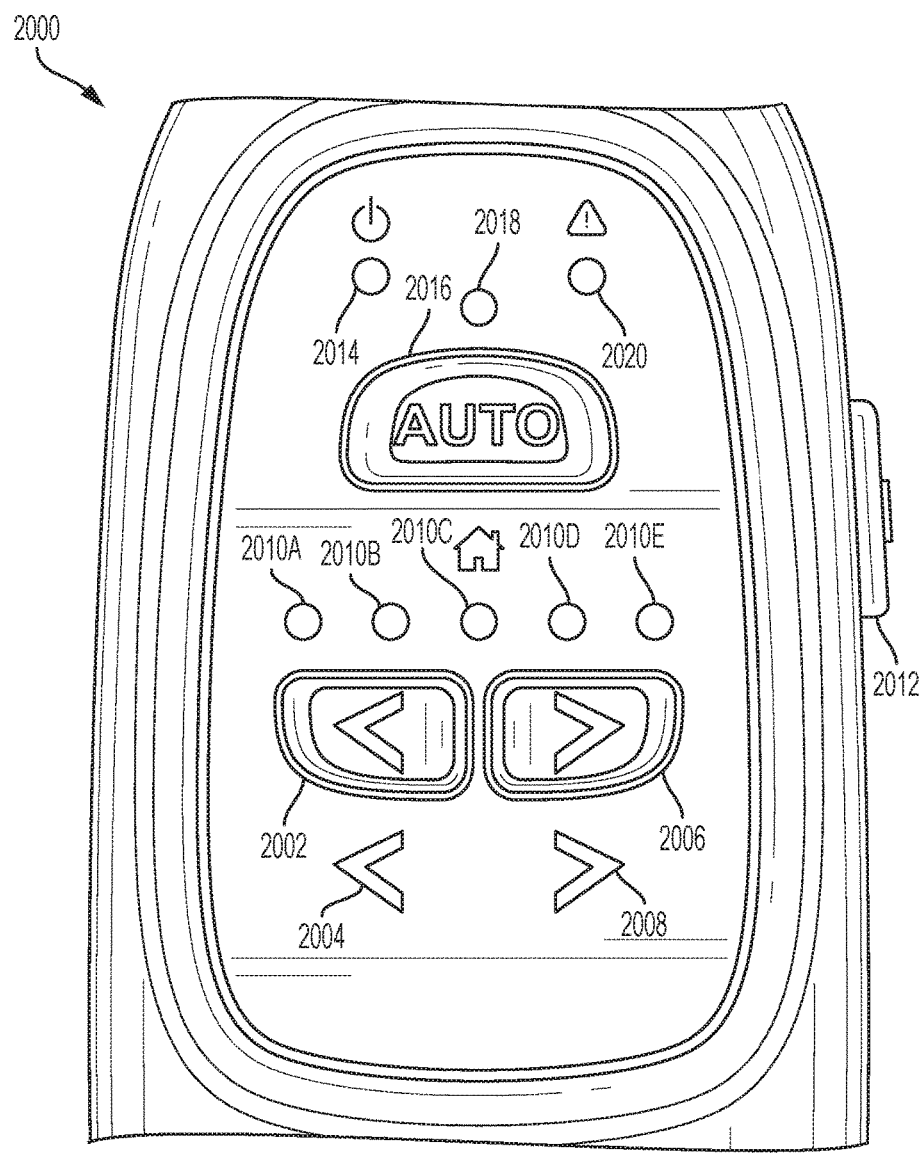
FIG. 20 is an illustration of another exemplary control panel of a laser ablation catheter.

FIG. 20 illustrates an exemplary control panel 2000 of a laser ablation catheter, such as the laser ablation catheter 800 described above. That is, the laser ablation catheter 800 may include the control panel 2000 in lieu of the control panel 860 described above. Components of the laser ablation catheter 800 are referenced in the following description for illustrative purposes, although it is to be understood that the control panel 2000 may be used with other laser ablation catheters.

The control panel 2000 facilitates clinician control of the laser ablation catheter. The control panel 2000 includes several clinician-operable inputs and/or indicators that are operatively coupled to the catheter controller 848.

The control panel 2000 includes a first input 2002 (for example, a button) that may be actuated by the clinician to actuate the prime mover 840. That is, the clinician may press the first input 2002 to cause the catheter controller 848 to actuate the prime mover 840 and thereby rotate the drive wire 830 and the distal tip 808 of the sheath 810. In addition, pressing the first input 2002 actuates the prime mover 840 in a manner that rotates the drive wire 830 and the distal tip 808 of the sheath 810 in a first direction (for example, clockwise when facing the distal tip 808). The control panel 2000 includes a first visual indicator 2004 (for example, a light-emitting diode) that indicates when the first input 2002 is actuated and the prime mover 840, the drive wire 830, and the distal tip 808 of the sheath 810 are rotating in the first direction.

The control panel 2000 includes a second input 2006 (for example, a button) that may be actuated by the clinician to actuate the prime mover 840. That is, the clinician may press the second input 2006 to cause the catheter controller 848 to actuate the prime mover 840 and thereby rotate the drive wire 830 and the distal tip 808 of the sheath 810. In addition, pressing the second input 2006 actuates the prime mover 840 in a manner that rotates the drive wire 830 and the distal tip 808 of the sheath 810 in a second direction (for example, counterclockwise when facing the distal tip 808). The control panel 2000 includes a second visual indicator 2008 (for example, a light-emitting diode) that indicates when the second input 2006 is actuated and the prime mover 840, the drive wire 830, and the distal tip 808 of the sheath 810 are rotating in the second direction.

The control panel 2000 further includes a plurality of visual indicators, such as a third visual indicator 2010A (for example, a light-emitting diode), a fourth visual indicator 2010B (for example, a light-emitting diode), a fifth visual indicator 2010C (for example, a light-emitting diode), a sixth visual indicator 2010D (for example, a light-emitting diode), and a seventh visual indicator 2010E (for example, a light-emitting diode). The visual indicators may be energized (for example, illuminated) based on the rotational position of the prime mover 840 (as determined by the rotational position sensor 852), the proximal end of the drive wire 830, and, generally, the distal end of the drive wire 830 and the distal tip 808 of the sheath 810.

For example, one or more of the visual indicators may be energized when the rotational position of the prime mover 840 reaches or passes a specific threshold, and one of the visual indicators may be energized when the rotational position of the prime mover 840 has not reached a threshold. As a specific example, the prime mover 840 may have a "home" position in which the drive wire 830 and the distal end of the sheath 810 are not rotated relative to the housing 806. From the home position, the prime mover 840 may rotate over an angle α (for example, 2160 degrees) in a first direction (that is, the prime mover 840 may rotate until it reaches a first rotational limit, referred to here as +α). The first direction may be, for example, clockwise when facing the distal tip 808. Similarly, from the home position the prime mover 840 may rotate over the angle α in a second direction (that is, the prime mover 840 may rotate until it reaches a second rotational limit, referred to here as −α). The second direction may be, for example, counterclockwise when facing the distal tip 808. As such, the rotational range of the prime mover 840 is 2α (for example, 4320 degrees). The rotational position of the prime mover 840 is referred to here as β and the home position is defined as β=0. As such, β is positive when the rotational position of the prime mover 840 is closer to the first rotational limit than the second rotational limit and β is negative when the rotational position of the prime mover 840 is closer to the second rotational limit than the first rotational limit. With this definition, the visual indicator thresholds may be +α, +0.5α, −0.5α, −α, and the visual indicators may be energized, as follows:

third visual indicator 2010A: β=+α
fourth visual indicator 2010B: +α>β≥+0.5α
fifth visual indicator 2010C: +0.5α>β>−0.5α
sixth visual indicator 2010D: −0.5α≥β>−α
seventh visual indicator 2010E: β=−α

Stated another way, for example, the third visual indicator 2010A is energized when the rotational position of the prime mover 840 is 2160 degrees (that is, β=2160 degrees) and the seventh visual indicator 2010E is energized when the rotational position of the prime mover 840 is −2160 degrees (that is, β=−2160 degrees).

As another example, each visual indicator may correspond to a portion of the rotational range of the prime mover 840, and each visual indicator may be energized when the prime mover 840 is rotationally positioned with its specific portion of the rotational range. As a specific example, the prime mover 840 may have a "home" position in which the drive wire 830 and the distal end of the sheath 810 are not rotated relative to the housing 806. From the home position, the prime mover 840 may rotate over an angle α (for example, 2160 degrees) in a first direction (that is, the prime mover 840 may rotate until it reaches a first rotational limit, referred to here as +α). The first direction may be, for example, clockwise when facing the distal tip 808. Similarly, from the home position the prime mover 840 may rotate over the angle α in a second direction (that is, the prime mover 840 may rotate until it reaches a second rotational limit, referred to here as −α). The second direction may be, for example, counterclockwise when facing the distal tip 808. As such, the rotational range of the prime mover 840 is 2α (for example, 4320 degrees). The rotational position of the prime mover 840 is referred to here as β and the home position is defined as β=0. As such, β is positive when the rotational position of the prime mover 840 is closer to the first rotational limit than the second rotational limit and β is negative when the rotational position of the prime mover 840 is closer to the second rotational limit than the first rotational limit. With this definition, the visual indicators may be energized when the rotational position of the prime mover 840 is as follows:

third visual indicator 2010A: +α≥β>+0.75α
fourth visual indicator 2010B: +0.75α≥β>+0.25α
fifth visual indicator 2010C: +0.25α≥β≥−0.25α
sixth visual indicator 2010D: −0.25α>β≥−0.75α
seventh visual indicator 2010E: −0.75α>β≥−α

With the previous definition and as another example, the visual indicators may be energized when the rotational position of the prime mover 840 is as follows:

third visual indicator 1910A: +α≥β≥+(⅝)α
fourth visual indicator 1910B: +(⅝)α>β>+(⅛)α
fifth visual indicator 1910C: +(⅛)α≥β≥−(⅛)α
sixth visual indicator 1910D: −(⅛)α>β>−(⅝)α
seventh visual indicator 1910E: −(⅝)α≥β≥−α

With the previous definition and as yet another example, the visual indicators may be energized when the rotational position of the prime mover 840 is as follows:

third visual indicator 1910A: +α≥β≥+(⅝)α
fourth visual indicator 1910B: +(⅝)α>β>+(⅓)α
fifth visual indicator 1910C: +(⅓)α≥β≥−(⅓)α
sixth visual indicator 1910D: −(⅓)α>β>−(⅝)α
seventh visual indicator 1910E: −(⅝)α≥β≥−α

The control panel 2000 further includes a third input 2012 (for example, a button) that may be actuated by the clinician to cause the laser ablation catheter 800 to turn "on" and "off". When the laser ablation catheter 800 is "on", the inputs 2002 and 2006 may be actuated to cause the catheter controller 848 to actuate the prime mover 840 as described above. When the laser ablation catheter 800 is "off", the catheter controller 848 does not actuate the prime mover 840 when the inputs 2002 and 2006 are actuated. In some embodiments, the control panel 2000 includes an eighth visual indicator 2014 (for example, a light-emitting diode) that indicates when the laser ablation catheter 800 is "on".

The control panel 2000 includes a fourth input 2016 (for example, a button). The fourth input 2016 may be actuated by the clinician to cause the laser ablation catheter 800 to enter an automatic mode. In the automatic mode, the catheter controller 848 automatically controls actuation of the prime mover 840 and, as a result, rotation of the drive wire 830 and the distal tip 808 of the sheath 810. Specifically, the catheter controller 848 actuates the prime mover 840 only when the sensor 854 detects laser energy is being emitted from the transport members 804. In some embodiments and when the laser ablation catheter 800 is in the automatic mode, the fourth input 2016 may be actuated by the clinician to cause the laser ablation catheter 800 to exit the automatic mode. The control panel 2000 includes a ninth visual indicator 2018 (for example, a light-emitting diode) that indicates when the laser ablation catheter 800 is in the automatic mode.

In some embodiments, the fourth input 2016 may be actuated by the clinician to cause the laser ablation catheter 800 to enter a "watching" mode. In the watching mode, the catheter controller 848 actuates the prime mover 840 when (1) the sensor 854 detects laser energy is being emitted from the transport members 804 and (2) one of the first input 2002 and the second input 2006 is actuated (to cause rotation of the distal tip 808 of the sheath 810 in the first and second directions, respectively). In some embodiments and when the laser ablation catheter 800 is in the watching mode, the fourth input 2016 may be actuated by the clinician to cause the laser ablation catheter 800 to exit the watching mode. The ninth visual indicator 2018 may indicate when the laser ablation catheter 800 is in the watching mode.

In some embodiments, the control panel 2000 includes a tenth visual indicator 2020 (for example, a light-emitting diode) that indicates the presence of a device error or fault condition (for example, as detected by the catheter controller 848). For example, device errors and fault conditions may include the prime mover 840 rotating past a rotational limit, a reduction in power to the prime mover 840, and the prime mover 840 failing to rotate in response to actuation of one or more of the inputs 2002 and 2006.

In some embodiments, catheters according to the present disclosure may include other types of prime movers for rotating the drive wire other than an electric motor. Such other types of prime movers may be, for example, fluid-driven motors and/or pneumatic or hydraulic components. Replacing the electric or electronic components, including a battery to drive the electric or electronic components, with pneumatic or hydraulic components reduces the potential difficulties associated with sterilizing a medical device containing such electric or electronic components.

Figure 21:
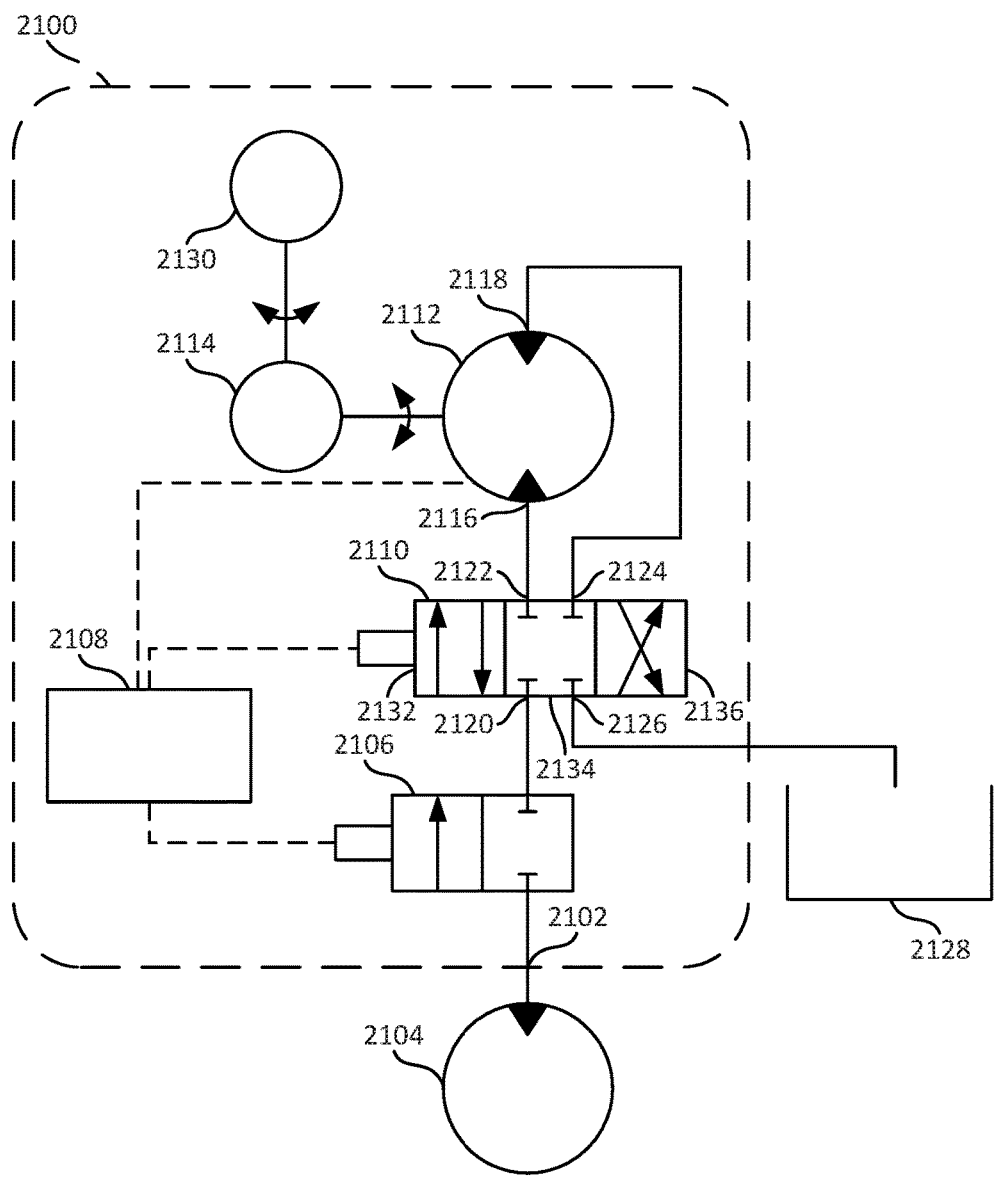
FIG. 21 is a circuit diagram of an exemplary laser ablation catheter including pneumatic components.

As an example and referring to FIG. 21, an embodiment of a laser ablation catheter 2100 according to the present disclosure of is illustrated. The laser ablation catheter 2100 may be generally the same or similar to any of the laser ablation catheters described herein (for example, the laser ablation catheter 800), except that the laser ablation catheter 2100 includes pneumatic components to rotate the drive wire 2130. The laser ablation catheter 2100 includes a first port 2102 for detachably coupling to and receiving a pneumatic fluid (for example, a compressed gas, such as air or carbon dioxide) from a regulated pneumatic fluid source 2104 (for example, a compressed air conduit in a building or a disposable cartridge). In some embodiments, the first port 2102 is coupled to a stop valve 2106 that may be actuated to selectively inhibit flow of the pneumatic fluid through the pneumatic components. Specifically, as shown in the figures, the stop valve 2106 may be a two-way, two-position valve. In some embodiments, the stop valve 2106 may be operatively coupled to and actuated by a controller 2108, which may be any of the controllers described herein. The stop valve 2106 is coupled to a directional control valve 2110, which is in turn coupled to a fluid-driven motor 2112 (that is, a motor that converts fluid motion into mechanical rotation). The fluid-driven motor 2112 is coupled to and rotatably drives a speed reducer 2114 (for example, a gearbox), which in turn rotatably drives the drive wire 2130.

Continuing to refer to FIG. 21, the directional control valve 2110 selectively delivers the pneumatic fluid to the fluid-driven motor 2112 via a first inlet/outlet port 2116 and permits the fluid-driven motor 2112 to discharge the fluid via a second inlet/outlet port 2118 to rotate the fluid-driven motor 2112 and the drive wire 2130 in a first direction. The directional control valve 2110 also selectively delivers the pneumatic fluid to the fluid-driven motor 2112 via the second inlet/outlet port 2118 and permits the fluid-driven motor 2112 to discharge the fluid via the first inlet/outlet port 2116 to rotate the fluid-driven motor 2112 and the drive wire 2130 in a second direction opposite the first direction.

In some embodiments, the directional control valve 2110 is a four-way valve that includes (1) a first port 2120 coupled to the stop valve 2106; (2) a second port 2122 coupled to the first inlet/outlet port 2116; (3) a third port 2124 coupled to the second inlet/outlet port 2118; and (4) a fourth port 2126 for delivering the pneumatic fluid to a reservoir 2128 (for example, discharging the fluid to atmosphere). In some embodiments, such as those in which the stop valve 2106 is omitted, the directional control valve 2110 may be a four-way, three-position valve. In such embodiments, the directional control valve 2110 includes (1) a first position 2132 in which the valve 2110 delivers the fluid to the first inlet/outlet port 2116 to rotate the fluid-driven motor 2112 and the drive wire 2130 in the first direction; (2) a second position 2134, or stop position, in which the valve 2110 inhibits flow of the fluid through the fluid-driven motor 2112; and (3) a third position 2136 in which the valve 2110 delivers the fluid to the second inlet/outlet port 2118 to rotate the fluid-driven motor 2112 and the drive wire 2130 in the second direction.

In other embodiments, such as those in which the stop valve 2106 is present, the directional control valve 2110 may be a four-way, two-position valve, and the second position 2134 may be omitted. In some embodiments, the directional control valve 2110 may be operatively coupled to and actuated by the controller 2108, and the controller 2108 may actuate the valve 2110 such that the catheter 2100 is operable in any of the modes described herein (for example, the manual drive mode, the automatic mode, or the watching mode). In addition, the controller 2108 may energize one or more of the visual indicators, such as any of the indicators described herein, based on a rotational position of the fluid-driven motor 2112 relative to the catheter housing.

Figure 22:
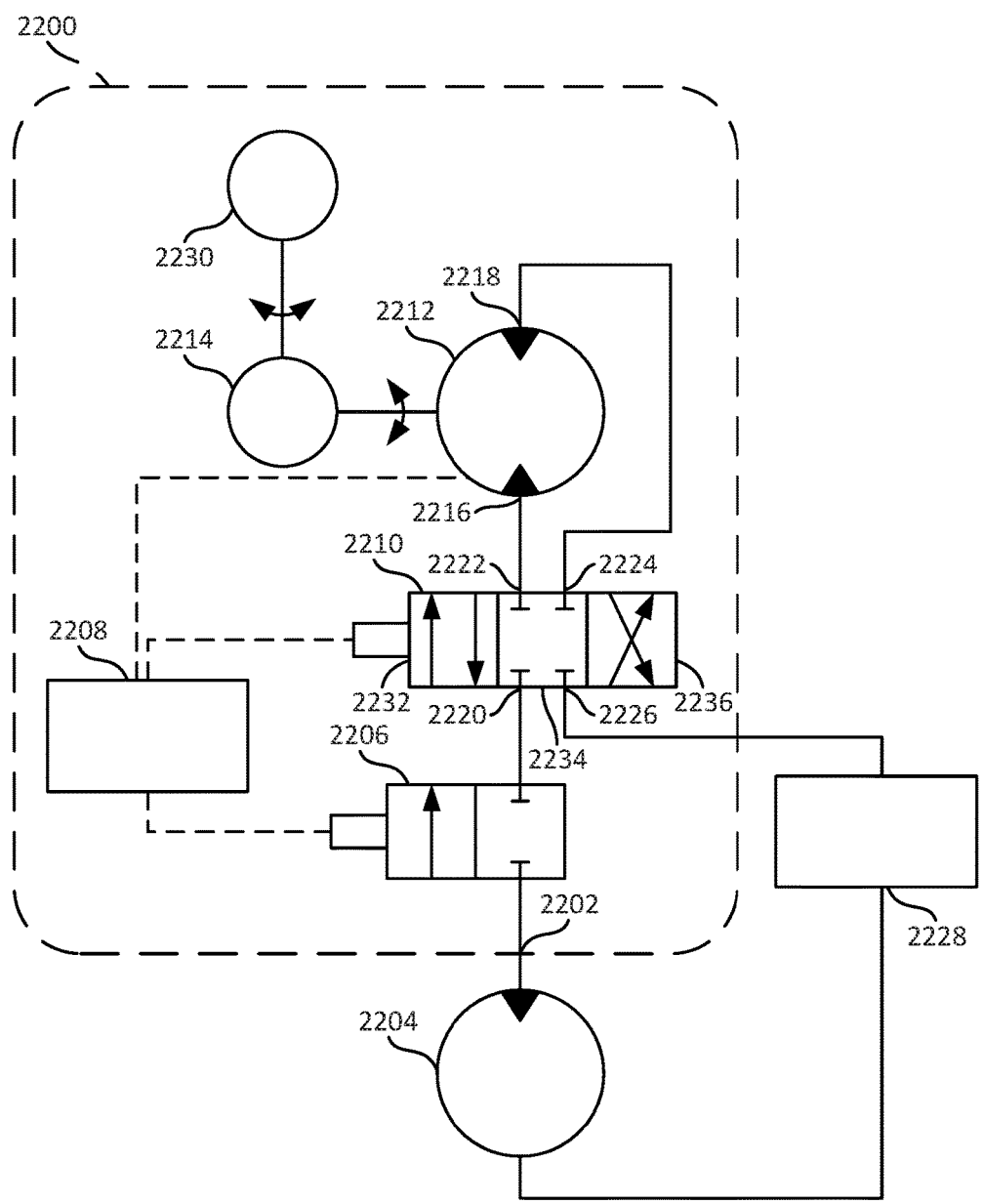
FIG. 22 is a circuit diagram of an exemplary laser ablation catheter including hydraulic components.

Referring to FIG. 22, another example of an embodiment of a laser ablation catheter 2200 according to the present disclosure of is illustrated. The laser ablation catheter 2200 may be generally the same or similar to any of the laser ablation catheters described herein (for example, the laser ablation catheter 800), except that the laser ablation catheter 2200 includes hydraulic components to rotate the drive wire 2230. The laser ablation catheter 2200 includes a first port 2202 for detachably coupling to and receiving a hydraulic fluid (for example, a pressurized liquid) from a hydraulic fluid source 2204 (for example, a pump). In some embodiments, the first port 2202 is coupled to a stop valve 2206 that may be actuated to selectively inhibit flow of the hydraulic fluid through the hydraulic components. Specifically, as shown in the figures, the stop valve 2206 may be a two-way, two-position valve. In some embodiments, the stop valve 2206 may be operatively coupled to and actuated by a controller 2208, which may be any of the controllers described herein. The stop valve 2206 is coupled to a directional control valve 2210, which is in turn coupled to a fluid-driven motor 2212 (that is, a motor that converts fluid motion into mechanical rotation). The fluid-driven motor 2212 is coupled to and rotatably drives a speed reducer 2214 (for example, a gearbox), which in turn rotatably drives the drive wire 2230.

Continuing to refer to FIG. 22, the directional control valve 2210 selectively delivers the hydraulic fluid to the fluid-driven motor 2212 via a first inlet/outlet port 2216 and permits the fluid-driven motor 2212 to discharge the fluid via a second inlet/outlet port 2218 to rotate the fluid-driven motor 2212 and the drive wire 2230 in a first direction. The directional control valve 2210 also selectively delivers the hydraulic fluid to the fluid-driven motor 2212 via the second inlet/outlet port 2218 and permits the fluid-driven motor 2212 to discharge the fluid via the first inlet/outlet port 2216 to rotate the fluid-driven motor 2212 and the drive wire 2230 in a second direction opposite the first direction.

In some embodiments, the directional control valve 2210 is a four-way valve that includes (1) a first port 2220 coupled to the stop valve 2206; (2) a second port 2222 coupled to the first inlet/outlet port 2216; (3) a third port 2224 coupled to the second inlet/outlet port 2218; and (4) a fourth port 2226 for delivering the hydraulic fluid to a reservoir 2228. The fluid source 2204 may receive hydraulic fluid from the reservoir 2228. In some embodiments, such as those in which the stop valve 2206 is omitted, the directional control valve 2210 may be a four-way, three-position valve. In such embodiments, the directional control valve 2210 includes (1) a first position 2232 in which the valve 2210 delivers the fluid to the first inlet/outlet port 2216 to rotate the fluid-driven motor 2212 and the drive wire 2230 in the first direction; (2) a second position 2234, or stop position, in which the valve 2210 inhibits flow of the fluid through the fluid-driven motor 2212; and (3) a third position 2236 in which the valve 2210 delivers the fluid to the second inlet/outlet port 2218 to rotate the fluid-driven motor 2212 and the drive wire 2230 in the second direction.

In other embodiments, such as those in which the stop valve 2206 is present, the directional control valve 2210 may be a four-way, two-position valve, and the second position 2234 may be omitted. In some embodiments, the directional control valve 2210 may be operatively coupled to and actuated by the controller 2208, and the controller 2208 may actuate the valve 2210 such that the catheter 2200 is operable in any of the modes described herein (for example, the manual drive mode, the automatic mode, or the watching mode). In addition, the controller 2208 may energize one or more visual indicators, such as any of the indicators described herein, based on a rotational position of the fluid-driven motor 2212 relative to the catheter housing.

Figure 23:
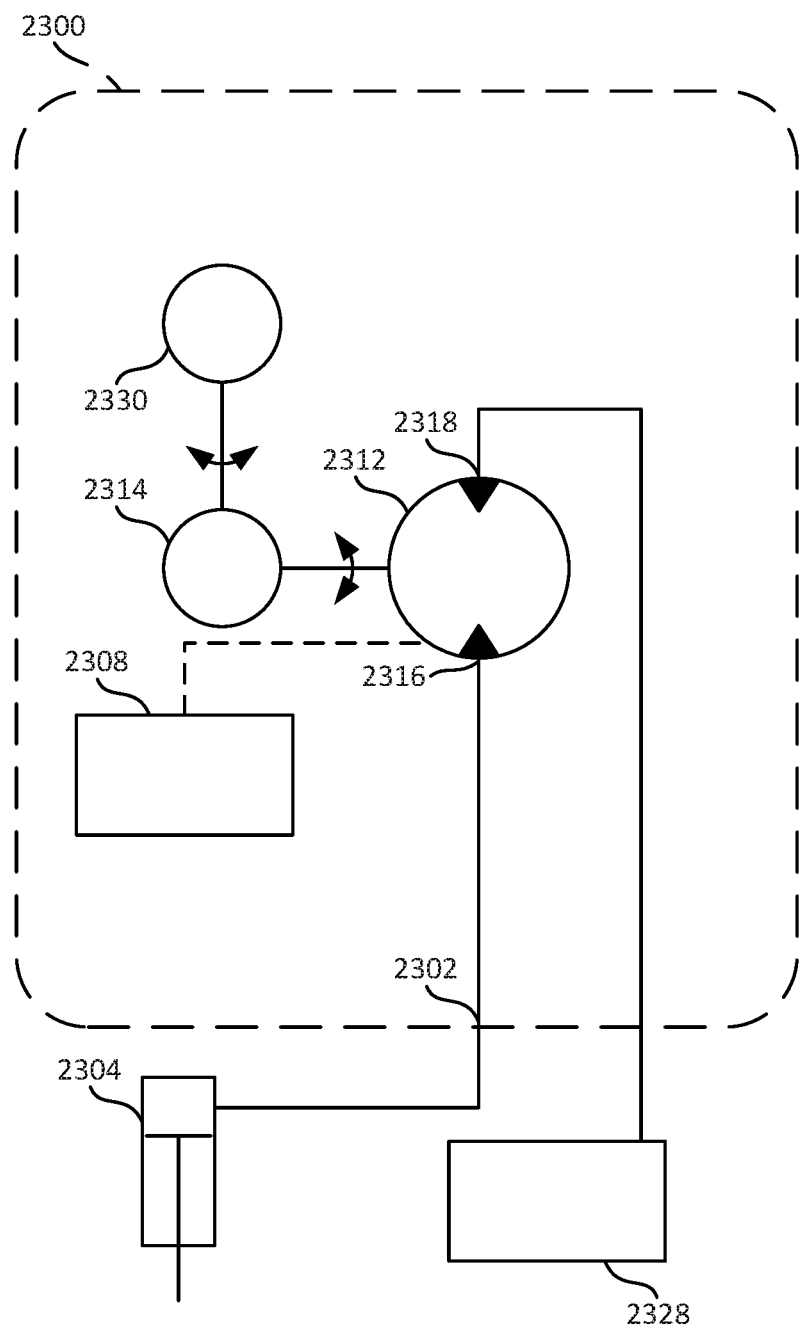
FIG. 23 is a circuit diagram of another exemplary laser ablation catheter including hydraulic components.

As yet another example and referring to FIG. 23, an embodiment of a laser ablation catheter 2300 according to the present disclosure of is illustrated. The laser ablation catheter 2300 may be generally the same or similar to any of the laser ablation catheters described herein (for example, the laser ablation catheter 800), except that the laser ablation catheter 2300 includes hydraulic components to rotate the drive wire 2330. The laser ablation catheter 2300 includes a first port 2302 for detachably coupling to and receiving a hydraulic fluid (for example, a liquid) from a hydraulic fluid source 2304 adapted to provide positive and negative pressure (for example, a syringe). The first port 2302 is coupled to a fluid-driven motor 2312 (that is, a motor that converts fluid motion into mechanical rotation). The fluid-driven motor 2312 is coupled to and rotatably drives a speed reducer 2314 (for example, a gearbox), which in turn rotatably drives the drive wire 2330. The hydraulic fluid source 2304 may be actuated in a first direction (for example, the plunger of the syringe may be pushed in) to deliver hydraulic fluid from the source 2304 to the fluid-driven motor 2312 via a first inlet/outlet port 2316 and discharge the fluid via a second inlet/outlet port 2318 to rotate the fluid-driven motor 2312 and the drive wire 2330 in a first direction. The discharged fluid is delivered to a reservoir 2328. The hydraulic fluid source 2304 may be actuated in a second direction (for example, the plunger of the syringe may be pulled out) to draw hydraulic fluid from the reservoir 2328 and deliver the fluid to the fluid-driven motor 2312 via the second inlet/outlet port 2318, and the fluid is discharged from the fluid-driven motor 2312 via the first inlet/outlet port 2316 to rotate the fluid-driven motor 2312 and the drive wire 2330 in a second direction opposite the first direction. A controller 2308, which may be any of the controllers described herein, may energize one or more visual indicators, such as any of the indicators described herein, based on a rotational position of the fluid-driven motor 2312 relative to the catheter housing.

In some embodiments, the systems and methods of this disclosure may be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein may be used to implement the various aspects of this disclosure. Exemplary hardware that may be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing may also be constructed to implement the methods described herein.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A laser energy delivery device for providing treatment to a subject,
the laser energy delivery device comprising:
a housing;
a coupling carried by the housing and adapted to couple to a laser energy generator;
a sheath carried by the housing, the sheath comprising a distal end adapted to be disposed in the subject;
a plurality of transport members carried by the sheath, the plurality of transport members adapted to receive laser energy at the coupling, transmit laser energy through the sheath, and deliver laser energy to the subject;
wherein at least one of the plurality of transport members comprises a bend formed between the proximal end and the distal end, and
the sensor is adapted to detect emission of laser energy at the bend;
a controller carried by the housing;
a fluid-driven motor carried by the housing and adapted to be driven upon receiving a fluid from a fluid source;
a drive wire carried by the sheath and eccentrically coupled to the distal end of the sheath, the drive wire adapted to be rotatably driven by the fluid-driven motor and rotating to eccentrically rotate the distal end of the sheath, and a plurality of visual indicators carried by the housing, wherein the controller is adapted to energize the plurality of visual indicators based on a rotational position of the fluid-driven motor relative to the housing.

2. The laser energy delivery device of claim 1, wherein the controller is adapted to energize at least one of the visual indicators when the rotational position of the fluid-driven motor reaches a threshold.

3. The laser energy delivery device of claim 1, wherein each visual indicator of the plurality of visual indicators corresponds to a portion of a rotational range of the fluid-driven motor, and wherein the controller is adapted to energize each visual indicator when the rotational position of the fluid-driven motor is within the portion of the rotational range of each visual indicator.

4. The laser energy delivery device of claim 1, further comprising a sensor adapted to detect transmission of laser energy through at least one of the plurality of transport members.

5. The laser energy delivery device of claim 4, wherein the sensor is adapted to send a signal in response to detecting transmission of laser energy through the at least one of the plurality of transport members, wherein the controller is adapted to receive the signal from the sensor, and further comprising an ancillary device adapted to augment treatment of the subject via the laser energy delivery device, the controller actuating the ancillary device upon receiving the signal from the sensor.

6. The laser energy delivery device of claim 5, wherein the ancillary devices comprise:

the fluid-driven motor; and the drive wire eccentrically coupled to the distal end of the sheath and adapted to be rotatably driven by the fluid-driven motor, the drive wire rotating to eccentrically rotate the distal end of the sheath.

7. The laser energy delivery device of claim 5, wherein the at least one of the plurality of transport members extends from a proximal end to a distal end, and the sensor is adapted to detect emission of laser energy at a location on the at least one of the plurality of transport members disposed between the proximal end and the distal end.

8. The laser energy delivery device of claim 1, wherein the fluid-driven motor comprises a first inlet/outlet port and a second inlet/outlet port, the fluid-driven motor is adapted to receive the fluid via the first inlet/outlet port and discharge the fluid via the second inlet/outlet port to rotate the fluid-driven motor and the drive wire in a first direction, the fluid-driven motor is adapted to receive the fluid via the second inlet/outlet port and discharge the fluid via the first inlet/outlet port to rotate the fluid-driven motor and the drive wire in a second direction opposite the first direction.

9. The laser energy delivery device of claim 8, further comprising a directional control valve coupled to the fluid-driven motor, the directional control valve being adapted to selectively deliver the fluid to the first inlet/outlet port and the second inlet/outlet port of the fluid-driven motor to rotate the drive wire in the first direction and the second direction, respectively.

10. The laser energy delivery device of claim 9, wherein the controller is operatively coupled to the directional control valve to selectively deliver the fluid to the first inlet/outlet port and the second inlet/outlet port of the fluid-driven motor to rotate the drive wire in the first direction and the second direction, respectively.

11. The laser energy delivery device of claim 9, wherein the directional control valve is a four-way valve.

12. The laser energy delivery device of claim 1, further comprising a speed reducer coupling the fluid-driven motor to the drive wire.

13. The laser energy delivery device of claim 12, wherein the speed reducer is a gearbox.

* * * * *